(12) United States Patent
Petluri et al.

(10) Patent No.: US 10,701,775 B2
(45) Date of Patent: *Jun. 30, 2020

(54) METHODS FOR GENERATING MELATONIN-RESPONSE-TUNED WHITE LIGHT WITH HIGH COLOR RENDERING

(71) Applicant: EcoSense Lighting, Inc., Los Angeles, CA (US)

(72) Inventors: Raghuram L. V Petluri, Los Angeles, CA (US); Paul Kenneth Pickard, Los Angeles, CA (US)

(73) Assignee: EcoSense Lighting, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/049,452

(22) Filed: Jul. 30, 2018

(65) Prior Publication Data
US 2018/0338355 A1 Nov. 22, 2018

Related U.S. Application Data

(63) Continuation of application No. PCT/US2016/015435, filed on Jan. 28, 2016.

(51) Int. Cl.
*H05B 45/20* (2020.01)
*A61N 5/06* (2006.01)
(Continued)

(52) U.S. Cl.
CPC ........... *H05B 45/20* (2020.01); *A61N 5/0618* (2013.01); *F21K 9/62* (2016.08); *H01L 25/0753* (2013.01);
(Continued)

(58) Field of Classification Search
CPC ......... F21K 9/64; H01L 33/32; H01L 33/502; H01L 33/505; H01L 33/507;
(Continued)

(56) References Cited

U.S. PATENT DOCUMENTS

2009/0218960 A1* 9/2009 Lyons ................... H05B 45/48
315/297
2010/0174345 A1 7/2010 Ashdown
(Continued)

FOREIGN PATENT DOCUMENTS

WO WO 2017/131693 A1 8/2017

OTHER PUBLICATIONS

Ji Hye Oh, Healthy natural efficient and tunable lighting; Light: Science & Applications; Feb. 14, 2014 (Year: 2014).*
(Continued)

*Primary Examiner* — Henry Luong
(74) *Attorney, Agent, or Firm* — Baker Hostetler

(57) ABSTRACT

The present disclosure provides methods for generating tunable white light with controllable circadian energy performance. The methods use a plurality of LED strings to generate light with color points that fall within blue, yellow/green, red, and cyan color ranges, with each LED string being driven with a separately controllable drive current in order to tune the generated light output. Different light emitting modes can be selected that utilize different combinations of the plurality of LED strings in order to tune the generated white light.

18 Claims, 30 Drawing Sheets

| | Spectral Power Distribution for Wavelength Ranges (nm) | | | | | | | | | |
|---|---|---|---|---|---|---|---|---|---|---|
| blue color range | 380-420 | 421-460 | 461-500 | 501-540 | 541-580 | 581-620 | 621-660 | 661-700 | 701-740 | 741-780 |
| min | 0.3 | 100.0 | 20.9 | 15.2 | 25.3 | 26.3 | 15.4 | 5.9 | 2.3 | 1.0 |
| max | 8.1 | 100.0 | 196.1 | 35.6 | 40.5 | 70.0 | 80.2 | 20.4 | 7.8 | 2.3 |
| red color range | | | | | | | | | | |
| min | 0.0 | 2.1 | 2.0 | 1.4 | 8.7 | 48.5 | 100.0 | 1.8 | 0.5 | 0.3 |
| max | 14.8 | 157.8 | 6.7 | 12.2 | 20.5 | 102.8 | 100.0 | 74.3 | 29.5 | 9.0 |
| yellow/green color range | | | | | | | | | | |
| min | 0.0 | 1.0 | 4.2 | 56.6 | 100.0 | 80.5 | 48.4 | 12.6 | 3.2 | 1.0 |
| max | 1.1 | 25.3 | 52.7 | 77.5 | 100.0 | 123.4 | 144.9 | 88.8 | 34.4 | 10.5 |
| cyan color range | | | | | | | | | | |
| min | 0.1 | 0.5 | 39.6 | 100.0 | 62.0 | 41.6 | 23.1 | 6.6 | 1.8 | 0.6 |
| max | 0.7 | 1.6 | 58.6 | 100.0 | 80.4 | 59.9 | 57.1 | 35.0 | 13.5 | 4.1 |

(51) Int. Cl.
*F21K 9/62* (2016.01)
*H01L 25/075* (2006.01)
*H01L 33/50* (2010.01)
*F21Y 113/13* (2016.01)
*F21Y 115/10* (2016.01)

(52) U.S. Cl.
CPC .... *H01L 33/507* (2013.01); *A61N 2005/0626* (2013.01); *A61N 2005/0652* (2013.01); *A61N 2005/0656* (2013.01); *A61N 2005/0663* (2013.01); *F21Y 2113/13* (2016.08); *F21Y 2115/10* (2016.08)

(58) Field of Classification Search
CPC ..... H01L 25/0753; H05B 33/00; H05B 33/12; H05B 33/0857; H05B 37/00; H05B 37/02; F21V 9/00; F21V 9/08; F21V 9/10; F21Y 2113/13; F21Y 2103/10; F21Y 2115/10; A61N 5/0618; A61N 2005/0626; A61N 2005/0652; A61N 2005/0656; A61N 2005/0663; C09K 11/7734; C09K 11/7774
See application file for complete search history.

(56) References Cited

U.S. PATENT DOCUMENTS

| | | |
|---|---|---|
| 2011/0279015 A1 | 11/2011 | Negley et al. |
| 2012/0019127 A1 | 1/2012 | Hirosaki |
| 2012/0307487 A1 | 12/2012 | Eckel |
| 2013/0002157 A1* | 1/2013 | van de Ven ........ H05B 33/0824 315/192 |
| 2013/0002167 A1 | 1/2013 | Van de Ven |
| 2013/0049602 A1 | 2/2013 | Raj et al. |
| 2013/0249434 A1* | 9/2013 | Medendorp, Jr. .... C09K 11/586 315/294 |
| 2013/0258636 A1 | 10/2013 | Rettke |
| 2014/0159600 A1 | 6/2014 | Sutardja et al. |
| 2014/0217433 A1 | 8/2014 | Tudorica et al. |
| 2014/0217907 A1* | 8/2014 | Harris ................ H05B 33/0815 315/186 |
| 2014/0319560 A1* | 10/2014 | Tischler ................ H01L 33/502 257/98 |
| 2015/0002034 A1 | 1/2015 | Van de Ven et al. |

OTHER PUBLICATIONS

H. R. Davidson, Comparison of Munsell and MacAdam Color Space, vol. 48, pp. 606-608, 1958 (Year: 1958).*

Oh et al.; "Healthy, natural, efficient and tunable lighting: four-packaged white LEDs for optimizing the circadian effect, color quality and vision performance"; Light: Science & Applications; Feb. 2014; 30 pages.

Gall et al.; "Definition and Measurement of Circadian Radiometric Quantities"; CIE Symposium on Light and Health: Non-Visual Effects; 2004; 5 pages.

International Patent Application No. PCT/US2016/015435; Int'l Search Report and the Written Opinion; dated Mar. 31, 2016; 9 pages.

International Patent Application No. PCT/US2016/015435; Int'l Preliminary Report on Patentability; dated Aug. 9, 2018; 8 pages.

* cited by examiner

FIG. 7

| | Spectral Power Distribution for Wavelength Ranges (nm) | | | | |
|---|---|---|---|---|---|
| | 380-500 | 501-600 | 601-700 | 701-780 | |
| blue color range | | | | | |
| min | 100.0 | 27.0 | 24.8 | 1.1 | |
| max | 100.0 | 65.1 | 46.4 | 6.8 | |
| red color range | | | | | |
| min | 17.4 | 8.9 | 100.0 | 1.1 | |
| max | 3.3 | 24.8 | 100.0 | 18.1 | |
| yellow/green color range | | | | | |
| min | 35.8 | 100.0 | 61.2 | 7.9 | |
| max | 2.4 | 100.0 | 142.0 | 21.1 | |
| cyan color range | | | | | |
| min | 32.2 | 100.0 | 14.7 | 1.3 | |
| max | 19.9 | 100.0 | 42.4 | 6.1 | |

FIG. 8

| | Spectral Power Distribution for Wavelength Ranges (nm) | | | | | | | | | |
|---|---|---|---|---|---|---|---|---|---|---|
| | 380-420 | 421-460 | 461-500 | 501-540 | 541-580 | 581-620 | 621-660 | 661-700 | 701-740 | 741-780 |
| blue color range | | | | | | | | | | |
| min | 0.3 | 100.0 | 20.9 | 15.2 | 25.3 | 26.3 | 15.4 | 5.9 | 2.3 | 1.0 |
| max | 8.1 | 100.0 | 196.1 | 35.6 | 40.5 | 70.0 | 80.2 | 20.4 | 7.8 | 2.3 |
| red color range | | | | | | | | | | |
| min | 0.0 | 2.1 | 2.0 | 1.4 | 8.7 | 48.5 | 100.0 | 1.8 | 0.5 | 0.3 |
| max | 14.8 | 157.8 | 6.7 | 12.2 | 20.5 | 102.8 | 100.0 | 74.3 | 29.5 | 9.0 |
| yellow/green color range | | | | | | | | | | |
| min | 0.0 | 1.0 | 4.2 | 56.6 | 100.0 | 80.5 | 48.4 | 12.6 | 3.2 | 1.0 |
| max | 1.1 | 25.3 | 52.7 | 77.5 | 100.0 | 123.4 | 144.9 | 88.8 | 34.4 | 10.5 |
| cyan color range | | | | | | | | | | |
| min | 0.1 | 0.5 | 39.6 | 100.0 | 62.0 | 41.6 | 23.1 | 6.6 | 1.8 | 0.6 |
| max | 0.7 | 1.6 | 58.6 | 100.0 | 80.4 | 59.9 | 57.1 | 35.0 | 13.5 | 4.1 |

FIG. 9A

| Blue Channel Relative Intensity | Red Channel Relative Intensity | Yellow-Green Channel Relative Intensity | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 1 | 0.0339 | 0 | 0.4023 | 0.2933 | 0.3135 | 7931.21 | 5.68 | 91.61 | 70.84 | 99.92 | 97.94 | 275.05 | 248.49 | 272.80 | 0.99 |
| 0.8449 | 0.1018 | 0.0242 | 0.4055 | 0.3129 | 0.3333 | 6463.2 | 5.35 | 94.45 | 90.6 | 98.29 | 100.27 | 275.19 | 227.63 | 238.90 | 0.87 |
| 0.6543 | 0.0792 | 0 | 0.2955 | 0.3209 | 0.3407 | 6024.95 | 5.13 | 93.01 | 84.77 | 95.35 | 99.44 | 279.56 | 220.11 | 229.67 | 0.82 |
| 0.8384 | 0.0985 | 0.1341 | 0.3506 | 0.3312 | 0.3518 | 5552.28 | 5.97 | 90.58 | 73.58 | 90.88 | 98.52 | 286.63 | 208.37 | 214.16 | 0.74 |
| 0.4863 | 0.0889 | 0.1115 | 0.2052 | 0.3462 | 0.363 | 4997.1 | 5.2 | 91.16 | 78.81 | 87.76 | 99.81 | 286.58 | 195.85 | 193.16 | 0.67 |
| 0.6026 | 0.2504 | 0.1373 | 0.3667 | 0.3634 | 0.3759 | 4485.68 | 5.02 | 95.06 | 96.27 | 83.91 | 100.25 | 277.13 | 185.22 | 171.80 | 0.62 |
| 1 | 0.3473 | 0.4152 | 0.3118 | 0.3772 | 0.3745 | 4073.17 | -0.08 | 90.93 | 91.26 | 83.45 | 107.89 | 280.4 | 173.72 | 155.77 | 0.55 |
| 0.8578 | 0.6349 | 0.454 | 0.3247 | 0.404 | 0.3834 | 3467.6 | -2.94 | 92.63 | 90.11 | 78.37 | 116.41 | 266.14 | 158.07 | 127.94 | 0.48 |
| 0.5444 | 0.6349 | 0.3764 | 0.1826 | 0.427 | 0.3863 | 3023.73 | -5.88 | 92.19 | 85.42 | 73.89 | 128.76 | 254.8 | 144.95 | 107.19 | 0.42 |
| 0.4766 | 0.7415 | 0.5121 | 0.0404 | 0.4498 | 0.3933 | 2706.32 | -5.69 | 91.9 | 96.92 | 65.30 | 136.56 | 252.44 | 130.08 | 85.87 | 0.34 |
| 0.2666 | 0.8869 | 0.4249 | 0.0468 | 0.4763 | 0.3973 | 2386.25 | -5.7 | 92.72 | 92.51 | 55.96 | 149.19 | 237.16 | 116.80 | 67.67 | 0.29 |
| 0.1341 | 0.9095 | 0.3635 | 0 | 0.5003 | 0.3972 | 2129.89 | -5.81 | 93.17 | 96.64 | 47.58 | 164.25 | 225.01 | 104.75 | 53.12 | 0.24 |
| 0 | 1 | 0.273 | 0 | 0.5311 | 0.3941 | 1848.99 | -5.3 | 92.71 | 95.71 | 36.42 | 193.96 | 206.77 | 89.73 | 38.15 | 0.18 |

FIG. 9B

| Blue Channel Relative Intensity | Red Channel Relative Intensity | Yellow-Green Channel Relative Intensity | Cyan Channel OFF | ccx | ccy | CCT | duv | Ra | R9 | GAI | GAIBB | LER (Luminous efficacy of radiation) (lm/W) | melotonian suppressing mW per 100 lumens (radiation) | CER (Circadian efficacy of radiation) (blm/W) | CAF (Circadian action factor) (blm/lm) |
|---|---|---|---|---|---|---|---|---|---|---|---|---|---|---|---|
| 1 | 0 | 0.6414 | | 0.3732 | 0.3838 | 4246.95 | 5.48 | 76.14 | 28.02 | 74.82 | 98.42 | 316.1 | 168.16 | 155.67 | 0.49 |
| 0.8126 | 0.0953 | 0.4992 | | 0.3807 | 0.3771 | 3994.63 | 0.1 | 80.19 | 52.15 | 79.21 | 107.44 | 300.14 | 165.81 | 148.54 | 0.49 |
| 0.6931 | 0.2407 | 0.4895 | | 0.4012 | 0.3826 | 3525.22 | -2.68 | 84.42 | 73.43 | 77.31 | 116.26 | 285.51 | 154.74 | 126.99 | 0.44 |
| 0.4701 | 0.4507 | 0.4152 | | 0.4339 | 0.3863 | 2901.59 | -6.82 | 90.06 | 95.9 | 72.18 | 135.74 | 260.74 | 137.83 | 97.94 | 0.37 |
| 0.4346 | 0.5961 | 0.4669 | | 0.448 | 0.3926 | 2728.12 | -5.81 | 91.08 | 97.82 | 66.06 | 136.96 | 255.42 | 130.29 | 86.39 | 0.34 |
| 0.1986 | 0.525 | 0.3053 | | 0.4721 | 0.398 | 2442 | -5.34 | 92.4 | 97.64 | 56.90 | 144.78 | 242.94 | 118.12 | 69.22 | 0.28 |
| 0.1309 | 0.9031 | 0.3635 | | 0.5006 | 0.3977 | 2129.96 | -5.64 | 93.21 | 96.86 | 47.18 | 163.03 | 225.25 | 104.53 | 52.80 | 0.23 |
| 0.0112 | 1 | 0.273 | | 0.5298 | 0.3926 | 1849.65 | -5.83 | 92.67 | 95.73 | 37.72 | 197.94 | 206.51 | 90.49 | 39.02 | 0.19 |

FIG. 9C

| Blue Channel Relative Intensity | Red Channel Relative Intensity | Yellow-Green Channel OFF | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 0.7771 | 0.11 | | 0.412 | 0.3114 | 0.3346 | 6531.49 | 6.72 | 95.51 | 93.73 | 98.04 | 99.51 | 273.86 | 229.17 | 240.15 | 0.88 |
| 0.8611 | 0.1729 | | 0.5024 | 0.32 | 0.3418 | 6065.84 | 6.12 | 96.08 | 95.17 | 97.02 | 100.12 | 271.73 | 222.24 | 228.08 | 0.84 |
| 0.5638 | 0.1826 | | 0.3893 | 0.3341 | 0.3536 | 5435.84 | 5.61 | 95 | 81.84 | 94.42 | 100.77 | 268.52 | 210.92 | 208.39 | 0.78 |
| 0.4313 | 0.1922 | | 0.3441 | 0.3451 | 0.363 | 5036.18 | 5.64 | 93.47 | 74.75 | 91.28 | 100.44 | 266.32 | 202.59 | 194.24 | 0.73 |
| 0.7674 | 0.4637 | | 0.6801 | 0.3571 | 0.3682 | 4644.53 | 3.58 | 90.71 | 61.3 | 89.77 | 102.55 | 260.96 | 194.83 | 180.29 | 0.69 |
| 0.7221 | 0.7383 | | 0.8028 | 0.38 | 0.3775 | 4018.09 | 0.49 | 85.45 | 44.69 | 85.04 | 106.27 | 251.4 | 180.76 | 156.30 | 0.62 |
| 0.5574 | 0.832 | | 0.7027 | 0.3991 | 0.3786 | 3540.03 | -3.99 | 81.03 | 33.98 | 83.05 | 115.25 | 240.55 | 170.18 | 138.78 | 0.58 |
| 0.2181 | 0.6606 | | 0.4184 | 0.4298 | 0.3867 | 2976.19 | -6.11 | 76.72 | 31.56 | 73.05 | 123.89 | 228.3 | 152.96 | 113.41 | 0.50 |
| 0.3312 | 0.6737 | | 0.496 | 0.4566 | 0.395 | 2721.45 | -5.58 | 74.39 | 35.59 | 63.65 | 123.74 | 219.59 | 142.44 | 99.13 | 0.44 |

FIG. 9D

| | Blue, Red, and Cyan Channels | | | Blue, Red, and Yellow/Green Channels | | | Comparison of Emitting Modes | |
|---|---|---|---|---|---|---|---|---|
| CCT approx. | CCT | duv | Circadian Action Factor (CAF) | CCT | duv | Circadian Action Factor (CAF) | delta u'v' [pts] | Increase in Circadian Action Factor (CAF) |
| 4500 | 4644.53 | 3.58 | 0.69 | 4246.95 | 5.48 | 0.49 | 10.37 | 40.5% |
| 4000 | 4018.09 | 0.49 | 0.62 | 3994.63 | 0.1 | 0.49 | 0.65 | 26.0% |
| 3500 | 3540.03 | -3.99 | 0.58 | 3525.22 | -2.68 | 0.44 | 2.03 | 29.8% |
| 3000 | 2976.19 | -6.11 | 0.50 | 2901.59 | -6.82 | 0.37 | 2.92 | 32.5% |
| 2700 | 2721.45 | -5.58 | 0.44 | 2728.12 | -5.81 | 0.34 | 0.50 | 32.0% |

FIG. 10A

| Blue Channel Relative Intensity | Red Channel Relative Intensity | Yellow-Green Channel Relative Intensity | Cyan Channel Relative Intensity | ccx | ccy | CCT | duv | Ra | R9 | GAI | GAIBB | LER (Luminous efficacy of radiation) (lm/W) | melotonin suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 1 | 0.2052 | 0 | 0.4087 | 0.3118 | 0.3342 | 6513.44 | 6.33 | 95.31 | 88.73 | 96.16 | 98.28 | 272.78 | 228.13 | 239.71 | 0.871 |
| 1 | 0.2246 | 0.0404 | 0.4346 | 0.3219 | 0.3429 | 5971.36 | 5.77 | 95.96 | 92.96 | 94.40 | 98.95 | 274.14 | 218.77 | 225.57 | 0.816 |
| 0.7124 | 0.1179 | 0.0856 | 0.2859 | 0.3284 | 0.3485 | 5674.55 | 5.63 | 93.91 | 82.72 | 91.73 | 98.43 | 280.07 | 211.87 | 218.12 | 0.772 |
| 0.8708 | 0.1308 | 0.2116 | 0.3603 | 0.3452 | 0.3628 | 5030.37 | 5.47 | 93.03 | 79.08 | 86.66 | 98.37 | 284.84 | 197.16 | 196.50 | 0.685 |
| 0.7318 | 0.0889 | 0.2955 | 0.3021 | 0.3623 | 0.3761 | 4520.68 | 5.49 | 92.25 | 77.15 | 80.60 | 97.91 | 289.35 | 183.06 | 175.23 | 0.601 |
| 0.7964 | 0.0985 | 0.4475 | 0.2472 | 0.3809 | 0.3774 | 3991.84 | 0.18 | 92.31 | 84.12 | 80.03 | 105.98 | 284.32 | 171.13 | 155.40 | 0.543 |
| 0.8772 | 0.2439 | 0.6187 | 0.2795 | 0.4017 | 0.3829 | 3516.21 | -2.65 | 94.22 | 95.17 | 76.60 | 113.47 | 274.81 | 158.79 | 133.70 | 0.484 |
| 0.4443 | 0.1729 | 0.4733 | 0.0792 | 0.4311 | 0.3882 | 2966.56 | -5.66 | 92.96 | 91.07 | 69.74 | 127.78 | 267.1 | 140.45 | 105.43 | 0.393 |
| 0.2827 | 0.3247 | 0.3376 | 0.1341 | 0.4481 | 0.3938 | 2736.08 | -5.34 | 94.29 | 90.95 | 63.91 | 130.73 | 251.43 | 133.63 | 93.04 | 0.369 |
| 0.2633 | 0.3796 | 0.538 | 0.0436 | 0.4777 | 0.3989 | 2381.85 | -5.17 | 94.46 | 91.3 | 52.96 | 143.55 | 247.42 | 115.39 | 68.51 | 0.276 |
| 0.0372 | 0.1082 | 0.1179 | 0 | 0.5028 | 0.3991 | 2118.82 | -5.14 | 94.41 | 86.77 | 44.41 | 159.75 | 234.77 | 102.23 | 51.99 | 0.221 |
| 0 | 0.1082 | 0.0565 | 0 | 0.5426 | 0.3917 | 1752.2 | -5.08 | 94.58 | 81.56 | 31.75 | 206.81 | 206.71 | 83.16 | 33.12 | 0.160 |

FIG. 10B

| Blue Channel Relative Intensity | Red Channel Relative Intensity | Yellow-Green Channel Relative Intensity | Cyan Channel OFF | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 0.9192 | 0 | 1 | | 0.4226 | 0.3859 | 3102.17 | -5.38 | 86.41 | 69.93 | 70.83 | 124.61 | 282.19 | 142.196 | 110.937 | 0.391 |
| 0.5153 | 0.2213 | 0.7544 | | 0.4531 | 0.3928 | 2654.03 | -6.16 | 90.05 | 81.52 | 62.56 | 138.38 | 263.95 | 126.628 | 85.354 | 0.322 |
| 0.3183 | 0.3021 | 0.6026 | | 0.4734 | 0.3967 | 2415.98 | -5.83 | 91.87 | 84.42 | 55.37 | 146.52 | 252.67 | 116.369 | 70.280 | 0.277 |
| 0.189 | 0.4927 | 0.5477 | | 0.5009 | 0.397 | 2121.68 | -5.88 | 94.2 | 86.38 | 46.31 | 165.49 | 234.68 | 103.009 | 53.173 | 0.226 |
| 0 | 0.1082 | 0.0565 | | 0.5426 | 0.3917 | 1752.2 | -5.08 | 94.58 | 81.56 | 31.75 | 206.81 | 206.71 | 83.16 | 33.12 | 0.160 |

FIG. 10C

| Blue Channel Relative Intensity | Red Channel Relative Intensity | Yellow-Green Channel OFF | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 0.7771 | 0.11 | | 0.412 | 0.3114 | 0.3346 | 6531.49 | 6.72 | 95.51 | 93.73 | 98.04 | 99.51 | 273.86 | 229.17 | 240.15 | 0.878 |
| 0.8611 | 0.1729 | | 0.5024 | 0.32 | 0.3418 | 6065.84 | 6.12 | 96.08 | 95.17 | 97.02 | 100.12 | 271.73 | 222.24 | 228.08 | 0.839 |
| 0.5638 | 0.1826 | | 0.3893 | 0.3341 | 0.3536 | 5435.84 | 5.61 | 95 | 81.84 | 94.42 | 100.77 | 268.52 | 210.92 | 208.39 | 0.775 |
| 0.4313 | 0.1922 | | 0.3441 | 0.3451 | 0.363 | 5036.18 | 5.64 | 93.47 | 74.75 | 91.28 | 100.44 | 266.32 | 202.59 | 194.24 | 0.729 |
| 0.7674 | 0.4637 | | 0.6801 | 0.3571 | 0.3682 | 4644.53 | 3.58 | 90.71 | 61.3 | 89.77 | 102.55 | 260.96 | 194.83 | 180.29 | 0.690 |
| 0.7221 | 0.7383 | | 0.8028 | 0.38 | 0.3775 | 4018.09 | 0.49 | 85.45 | 44.69 | 85.04 | 106.27 | 251.4 | 180.76 | 156.30 | 0.621 |
| 0.5574 | 0.832 | | 0.7027 | 0.3991 | 0.3786 | 3540.03 | -3.99 | 81.03 | 33.98 | 83.05 | 115.25 | 240.55 | 170.18 | 138.78 | 0.576 |
| 0.2181 | 0.6606 | | 0.4184 | 0.4298 | 0.3867 | 2976.19 | -6.11 | 76.72 | 31.56 | 73.05 | 123.89 | 228.3 | 152.96 | 113.41 | 0.496 |
| 0.147 | 0.8384 | | 0.4637 | 0.4491 | 0.3939 | 2721.65 | -5.39 | 75.03 | 34.12 | 63.65 | 123.74 | 222.55 | 142.44 | 99.13 | 0.445 |

FIG 10D

|  | Blue, Red, and Cyan Channels | | | Blue, Red, and Yellow/Green Channels | | | Comparison of Emitting Modes | |
| --- | --- | --- | --- | --- | --- | --- | --- | --- |
| CCT approx. | CCT | duv | Circadian Action Factor (CAF) | CCT | duv | Circadian Action Factor (CAF) | delta u'v' [pts] | Increase in Circadian Action Factor (CAF) |
| 3000 | 2976.19 | -6.11 | 0.496 | 3102.17 | -5.38 | 0.391 | 4.65 | 26.8% |
| 2700 | 2721.65 | -5.39 | 0.445 | 2654.03 | -6.16 | 0.322 | 3.16 | 38.2% |

FIG. 11A

| Blue Channel Relative Intensity | Red Channel Relative Intensity | Yellow-Green Channel Relative Intensity | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 1 | 0 | 0.3861 | 0.1405 | 0.3127 | 0.3325 | 6477.11 | 5.02 | 87.94 | 70.23 | 87.00 | 88.77 | 280.35 | 227.519 | 251.914 | 0.894 |
| 0.7318 | 0.0436 | 0.2698 | 0.1696 | 0.3217 | 0.3426 | 5982.34 | 5.74 | 89.86 | 82.66 | 86.32 | 90.15 | 278.11 | 219.765 | 236.230 | 0.847 |
| 0.7512 | 0.0953 | 0.3118 | 0.1955 | 0.3322 | 0.3508 | 5513.86 | 5.05 | 91.38 | 88.93 | 85.07 | 91.66 | 277.39 | 210.747 | 220.437 | 0.792 |
| 1 | 0.1922 | 0.6478 | 0.2116 | 0.3445 | 0.3626 | 5056.25 | 5.69 | 91.11 | 76.87 | 80.63 | 91.42 | 284.71 | 198.216 | 202.695 | 0.709 |
| 0.7318 | 0.3312 | 0.6478 | 0.211 | 0.3644 | 0.3777 | 4465.89 | 5.52 | 92.3 | 87.35 | 75.89 | 92.83 | 282.76 | 183.251 | 175.813 | 0.619 |
| 0.5703 | 0.4507 | 0.7092 | 0 | 0.3794 | 0.3763 | 4023.34 | 0.09 | 93.08 | 93.9 | 76.80 | 101.25 | 276.87 | 172.874 | 157.692 | 0.567 |
| 0.4087 | 0.7092 | 0.664 | 0 | 0.405 | 0.3845 | 3455.19 | -2.66 | 95.61 | 89.93 | 72.48 | 109.79 | 264.05 | 157.839 | 130.114 | 0.490 |
| 0.2407 | 0.7351 | 0.4475 | 0 | 0.4276 | 0.3879 | 3027.61 | -5.28 | 94.8 | 79.33 | 68.79 | 122.04 | 250.14 | 145.703 | 109.232 | 0.434 |
| 0.1147 | 0.706 | 0.315 | 0.0145 | 0.449 | 0.3947 | 2729.73 | -5.08 | 93.17 | 76.75 | 61.48 | 128.21 | 241.06 | 134.158 | 91.238 | 0.376 |
| 0.0533 | 0.8094 | 0.2569 | 0.0145 | 0.472 | 0.3984 | 2446.73 | -5.17 | 91.5 | 76.37 | 53.79 | 137.85 | 230 | 122.329 | 74.377 | 0.322 |
| 0 | 0.8481 | 0.1535 | 0 | 0.5058 | 0.3989 | 2089.92 | -5.13 | 90.03 | 81.03 | 43.12 | 160.17 | 212.58 | 105.796 | 53.956 | 0.252 |
| 0 | 1 | 0.0792 | 0 | 0.5351 | 0.3935 | 1815.89 | -5.17 | 89.19 | 89.17 | 33.72 | 197.47 | 195.27 | 90.952 | 39.155 | 0.200 |

FIG. 11B

| Blue Channel Relative Intensity | Red Channel Relative Intensity | Yellow-Green Channel Relative Intensity | Cyan Channel OFF | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 1 | 0.0275 | 0.7092 | | 0.329 | 0.3483 | 5648.61 | 5.24 | 85.45 | 49.99 | 82.00 | 89.04 | 293.86 | 208.703 | 226.833 | 0.769 |
| 1 | 0.0533 | 0.79 | | 0.3342 | 0.3541 | 5431.83 | 5.78 | 85.46 | 49.6 | 80.56 | 89.18 | 295.49 | 203.718 | 218.485 | 0.737 |
| 1 | 0.1696 | 0.9838 | | 0.3474 | 0.365 | 4961.34 | 5.71 | 85.92 | 56.75 | 78.16 | 90.65 | 295.12 | 192.941 | 198.687 | 0.671 |
| 0.6672 | 0.2601 | 0.8611 | | 0.3625 | 0.3763 | 4516.32 | 5.52 | 87.57 | 65.79 | 75.00 | 92.20 | 293.19 | 181.688 | 177.601 | 0.603 |
| 0.5703 | 0.4507 | 0.7092 | | 0.3975 | 0.376 | 4021 | -0.07 | 93.08 | 94 | 76.95 | 101.48 | 276.72 | 172.876 | 157.695 | 0.567 |
| 0.4087 | 0.7092 | 0.664 | | 0.405 | 0.3844 | 3453.75 | -2.71 | 95.61 | 89.92 | 72.68 | 110.29 | 264 | 157.766 | 129.973 | 0.490 |
| 0.2407 | 0.7351 | 0.4475 | | 0.4277 | 0.3875 | 3021.12 | -5.47 | 94.82 | 79.36 | 68.97 | 122.67 | 249.89 | 145.592 | 109.080 | 0.434 |
| 0.1147 | 0.706 | 0.315 | | 0.45 | 0.3932 | 2703.57 | -5.73 | 93.28 | 77.18 | 62.06 | 131.39 | 240 | 133.529 | 90.447 | 0.375 |
| 0.0501 | 1 | 0.3086 | | 0.4763 | 0.3981 | 2392.35 | -5.42 | 91.67 | 77.8 | 52.76 | 141.86 | 228.05 | 119.861 | 71.175 | 0.310 |
| 0 | 1 | 0.0792 | | 0.5058 | 0.3989 | 2089.92 | -5.13 | 90.03 | 81.03 | 43.12 | 160.17 | 212.58 | 105.796 | 53.956 | 0.252 |
| 0 | 0.8481 | 0.1535 | | 0.5351 | 0.3935 | 1815.89 | -5.17 | 89.19 | 89.17 | 33.72 | 197.47 | 195.27 | 90.952 | 39.155 | 0.200 |

FIG. 11C

| Blue Channel Relative Intensity | Red Channel Relative Intensity | Yellow-Green Channel | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 1 | 0.1179 | OFF | 0.4863 | 0.3125 | 0.3336 | 6481.37 | 5.67 | 80.98 | 49.53 | 94.22 | 92.91 | 250.74 | | | |
| 0.6995 | 0.1115 | | 0.3667 | 0.3207 | 0.3404 | 6038.54 | 5.12 | 80.95 | 45.98 | 92.89 | 93.59 | 250.7 | | | |
| 0.5669 | 0.1147 | | 0.3312 | 0.3289 | 0.3493 | 5648.96 | 5.73 | 81.41 | 46.81 | 90.12 | 93.20 | 252.06 | 222.179 | 222.423 | 0.880 |
| 0.8417 | 0.2536 | | 0.5669 | 0.3433 | 0.3609 | 5096.58 | 5.35 | 81.46 | 44.72 | 86.53 | 93.68 | 251.74 | 210.327 | 203.799 | 0.808 |
| 0.399 | 0.1922 | | 0.3279 | 0.3625 | 0.3755 | 4510.53 | 5.13 | 80.6 | 40.6 | 80.18 | 93.27 | 250.65 | 195.413 | 180.402 | 0.717 |
| 0.5153 | 0.3764 | | 0.4378 | 0.3815 | 0.3784 | 3983.38 | 0.49 | 78.34 | 29.86 | 78.61 | 99.56 | 242.52 | 183.649 | 160.371 | 0.659 |
| 0.8708 | 0.9095 | | 0.7738 | 0.4004 | 0.3816 | 3535.52 | -2.95 | 76.69 | 25.97 | 75.66 | 106.67 | 235.2 | 172.094 | 141.931 | 0.601 |
| 0.3861 | 0.6995 | | 0.399 | 0.4309 | 0.389 | 2977.8 | -5.3 | 75.79 | 30.03 | 67.19 | 116.88 | 225.77 | 153.645 | 114.726 | 0.506 |
| 0.1638 | 0.3893 | | 0.1826 | 0.4461 | 0.3918 | 2749.64 | -5.95 | 75.82 | 34.36 | 62.43 | 122.88 | 220.95 | 144.730 | 102.345 | 0.461 |
| 0.0856 | 0.3538 | | 0.1212 | 0.4729 | 0.3977 | 2429.68 | -5.48 | 76.83 | 44.58 | 51.99 | 129.57 | 213.64 | 129.373 | 82.142 | 0.382 |
| 0.1341 | 1 | | 0.2246 | 0.4998 | 0.3981 | 2140.81 | -5.52 | 78.74 | 57.6 | 42.91 | 144.47 | 204.22 | 114.215 | 63.997 | 0.312 |
| 0.0436 | 1 | | 0.0727 | 0.5416 | 0.3914 | 1757.84 | -5.23 | 84.59 | 84.72 | 30.41 | 194.89 | 187.68 | 90.121 | 39.320 | 0.208 |

FIG 11D

| | Blue, Red, and Cyan Channels | | | Blue, Red, and Yellow/Green Channels | | | Comparison of Emitting Modes | |
|---|---|---|---|---|---|---|---|---|
| CCT approx. | CCT | duv | Circadian Action Factor (CAF) | CCT | duv | Circadian Action Factor (CAF) | delta u'v' [pts] | Increase in Circadian Action Factor (CAF) |
| 5500 | 5648.96 | 5.73 | 0.880 | 5431.83 | 5.78 | 0.737 | 3.58 | 19.4% |
| 5000 | 5096.58 | 5.35 | 0.808 | 4961.34 | 5.71 | 0.671 | 2.80 | 20.4% |
| 4500 | 4510.53 | 5.13 | 0.717 | 4516.32 | 5.52 | 0.603 | 0.48 | 18.9% |
| 4000 | 3983.38 | 0.49 | 0.659 | 4021 | -0.07 | 0.567 | 1.44 | 16.1% |
| 3500 | 3535.52 | -2.95 | 0.601 | 3453.75 | -2.71 | 0.490 | 2.68 | 22.6% |
| 3000 | 2977.8 | -5.3 | 0.506 | 3021.12 | -5.47 | 0.434 | 1.78 | 16.5% |
| 2700 | 2749.64 | -5.95 | 0.461 | 2703.57 | -5.73 | 0.375 | 2.22 | 23.0% |
| 2400 | 2429.68 | -5.48 | 0.382 | 2392.35 | -5.42 | 0.310 | 2.17 | 23.2% |
| 2100 | 2140.81 | -5.52 | 0.312 | 2089.92 | -5.13 | 0.252 | 3.83 | 23.6% |
| 1800 | 1757.84 | -5.23 | 0.208 | 1815.89 | -5.17 | 0.200 | 5.78 | 4.3% |

FIG. 12A

| Blue Channel Relative Intensity | Red Channel Relative Intensity | Yellow-Green Channel Relative Intensity | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 0.9806 | 0.0307 | 0.0081 | 0.3312 | 0.3119 | 0.3343 | 6507.3 | 6.33 | 87.57 | 92.75 | 91.06 | 90.81 | 288.15 | 235.267 | 272.607 | 0.935 |
| 0.8675 | 0.0404 | 0.0371 | 0.2989 | 0.3203 | 0.3436 | 6043.29 | 6.86 | 89.02 | 85.44 | 88.32 | 90.53 | 295.24 | 226.161 | 261.043 | 0.876 |
| 0.5121 | 0.0275 | 0.0598 | 0.1567 | 0.3311 | 0.3506 | 5556.87 | 5.41 | 90.37 | 76.49 | 85.55 | 91.00 | 302.28 | 215.400 | 247.264 | 0.810 |
| 0.6187 | 0.1341 | 0.0242 | 0.2892 | 0.3439 | 0.364 | 5083.21 | 6.63 | 90.27 | 82.33 | 82.10 | 90.77 | 303.99 | 206.186 | 231.444 | 0.750 |
| 0.9418 | 0.2666 | 0.1789 | 0.4023 | 0.3633 | 0.3771 | 4496.91 | 5.63 | 91.92 | 69.43 | 75.46 | 90.86 | 315.2 | 189.009 | 206.588 | 0.644 |
| 0.9418 | 0.4443 | 0.189 | 0.4023 | 0.3795 | 0.3761 | 4020.6 | 0.00 | 91.54 | 79.12 | 76.69 | 99.01 | 310.68 | 181.231 | 193.165 | 0.610 |
| 0.832 | 0.706 | 0.2246 | 0.4055 | 0.4043 | 0.3837 | 3464.76 | -2.85 | 90.92 | 76.32 | 71.46 | 106.20 | 310.96 | 166.544 | 168.828 | 0.531 |
| 0.6381 | 0.8578 | 0.3118 | 0.2763 | 0.4309 | 0.3891 | 2978.07 | -5.24 | 91.21 | 63.63 | 64.79 | 117.07 | 312.47 | 150.377 | 142.610 | 0.445 |
| 0.4572 | 0.8578 | 0.3506 | 0.1598 | 0.4503 | 0.3938 | 2702.89 | -5.56 | 92.05 | 51.3 | 58.46 | 124.20 | 314.69 | 138.570 | 123.191 | 0.381 |
| 0.2019 | 0.6414 | 0.2536 | 0.05 | 0.4749 | 0.3973 | 2402.59 | -5.68 | 91.54 | 37.72 | 50.43 | 135.32 | 313.95 | 124.914 | 100.560 | 0.311 |
| 0.0824 | 0.5574 | 0.1922 | 0.0112 | 0.5 | 0.3994 | 2147.5 | -5.12 | 89.81 | 24.74 | 42.12 | 147.34 | 310.53 | 112.347 | 80.124 | 0.250 |
| 0 | 0.4373 | 0.0921 | 0 | 0.5331 | 0.3943 | 1834.88 | -5.11 | 86.6 | 8.78 | 31.55 | 178.52 | 296.43 | 96.353 | 56.986 | 0.185 |

FIG. 12B

| Blue Channel Relative Intensity | Red Channel Relative Intensity | Yellow-Green Channel Relative Intensity | Cyan Channel OFF | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 1 | 0 | 0.6898 | | 0.3797 | 0.3886 | 4102.75 | 5.68 | 80.74 | 18.2 | 66.34 | 89.00 | 344.93 | 168.988 | 179.569 | 0.516 |
| 0.6252 | 0.05 | 0.3764 | | 0.3802 | 0.3767 | 4005.64 | 0.05 | 84.96 | 35.6 | 72.30 | 96.64 | 332.81 | 172.182 | 184.609 | 0.548 |
| 0.7092 | 0.2213 | 0.4992 | | 0.4022 | 0.3842 | 3515.75 | -2.18 | 87.35 | 39.72 | 68.71 | 103.97 | 331.83 | 159.522 | 161.787 | 0.480 |
| 0.8481 | 0.6898 | 0.7027 | | 0.4301 | 0.3875 | 2978.31 | -5.83 | 90.32 | 42.8 | 64.45 | 118.91 | 324.68 | 145.560 | 136.909 | 0.413 |
| 0.5024 | 0.7092 | 0.5346 | | 0.4508 | 0.3939 | 2704.64 | -5.15 | 90.37 | 37.42 | 57.34 | 124.10 | 324.3 | 134.593 | 117.360 | 0.353 |
| 0.1438 | 0.3861 | 0.2084 | | 0.4741 | 0.3988 | 2423.81 | -5.11 | 90.31 | 31.56 | 49.86 | 133.19 | 319.82 | 123.313 | 97.849 | 0.297 |
| 0.0921 | 0.8158 | 0.2666 | | 0.5083 | 0.3977 | 2058.39 | -5.45 | 88.84 | 19.85 | 39.58 | 155.97 | 307.68 | 107.787 | 73.207 | 0.230 |
| 0 | 0.4055 | 0.0953 | | 0.5298 | 0.3944 | 1859.98 | -5.31 | 86.84 | 9.52 | 30.88 | 165.12 | 298.31 | 96.875 | 56.844 | 0.182 |

FIG. 12C

| Blue Channel Relative Intensity | Red Channel Relative Intensity | Yellow-Green Channel | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 0.5057 | 0 | OFF | 0.1535 | 0.3037 | 0.3234 | 7073.59 | 5.02 | 86.19 | 90.76 | 94.26 | 91.55 | 281.27 | 245.096 | 284.801 | 1.001 |
| 1 | 0.0695 | | 0.3603 | 0.3174 | 0.3373 | 6206.97 | 5.31 | 87.43 | 93.32 | 91.06 | 91.88 | 288.84 | 230.956 | 266.131 | 0.910 |
| 0.7868 | 0.1308 | | 0.3376 | 0.3328 | 0.3514 | 5487.2 | 5.08 | 88.36 | 92.87 | 87.38 | 92.44 | 295.41 | 217.167 | 246.598 | 0.823 |
| 0.2084 | 0.0533 | | 0.1018 | 0.3442 | 0.3609 | 5063.91 | 4.99 | 88.92 | 90.67 | 84.23 | 92.65 | 299.65 | 207.870 | 232.810 | 0.765 |
| 0.5089 | 0.2213 | | 0.3086 | 0.3615 | 0.3752 | 4541.18 | 5.38 | 88.96 | 88.28 | 78.32 | 92.10 | 305.84 | 194.592 | 212.338 | 0.682 |
| 0.1793 | 0.1212 | | 0.1147 | 0.3797 | 0.3757 | 4013.92 | -0.24 | 86.91 | 93.49 | 78.20 | 99.70 | 302.09 | 184.895 | 196.265 | 0.636 |
| 0.5961 | 0.6834 | | 0.4604 | 0.404 | 0.3824 | 3459.12 | -3.39 | 85.15 | 91.68 | 73.05 | 106.95 | 301.32 | 170.783 | 173.338 | 0.561 |
| 0.4216 | 0.7641 | | 0.399 | 0.4258 | 0.3874 | 3056.03 | -5.22 | 83.45 | 86.09 | 67.28 | 114.40 | 300 | 158.718 | 153.734 | 0.498 |
| 0.2795 | 1 | | 0.4023 | 0.4536 | 0.3952 | 2665.83 | -5.27 | 81.87 | 74.09 | 57.14 | 120.13 | 299.31 | 143.594 | 129.074 | 0.417 |
| 0.1535 | 0.9386 | | 0.315 | 0.4719 | 0.3974 | 2440.05 | -5.52 | 80.52 | 64.93 | 50.90 | 126.11 | 296.99 | 134.239 | 114.149 | 0.371 |
| 0.0113 | 0.3215 | | 0.0824 | 0.4997 | 0.3997 | 2152.71 | -5.01 | 79.04 | 49 | 40.53 | 132.23 | 292.89 | 120.253 | 92.301 | 0.303 |

FIG 12D

| CCT approx. | Blue, Red, and Cyan Channels | | | Blue, Red, and Yellow/Green Channels | | | Comparison of Emitting Modes | |
|---|---|---|---|---|---|---|---|---|
| | CCT | duv | Circadian Action Factor (CAF) | CCT | duv | Circadian Action Factor (CAF) | delta u'v' [pts] | Increase in Circadian Action Factor (CAF) |
| 4500 | 4541.18 | 5.38 | 0.682 | 4102.75 | 5.68 | 0.516 | 10.80 | 32.1% |
| 4000 | 4013.92 | -0.24 | 0.636 | 4005.64 | 0.05 | 0.548 | 0.51 | 16.0% |
| 3500 | 3459.12 | -3.39 | 0.561 | 3515.75 | -2.18 | 0.480 | 2.02 | 16.8% |
| 3000 | 3056.03 | -5.22 | 0.498 | 2978.31 | -5.83 | 0.413 | 2.91 | 20.7% |
| 2700 | 2665.83 | -5.27 | 0.417 | 2704.64 | -5.15 | 0.353 | 1.82 | 18.2% |
| 2400 | 2440.05 | -5.52 | 0.371 | 2423.81 | -5.11 | 0.297 | 1.18 | 24.8% |
| 2100 | 2152.71 | -5.01 | 0.303 | 2058.39 | -5.45 | 0.230 | 6.94 | 31.9% |

FIG. 13A

| Blue Channel Relative Intensity | Red Channel Relative Intensity | Yellow-Green Channel Relative Intensity | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 1 | 0.05 | 0 | 0.2569 | 0.2783 | 0.2965 | 9804.25 | 5.73 | 87.11 | 34.54 | | | 281.95 | | | |
| 1 | 0.1147 | 0 | 0.3053 | 0.2874 | 0.3066 | 8561.51 | 5.44 | 90.77 | 53.75 | | | 286.89 | | | |
| 1 | 0.1502 | 0 | 0.3376 | 0.2922 | 0.3126 | 8027.91 | 5.79 | 92.34 | 60.8 | | | 289.87 | | | |
| 0.8869 | 0.231 | 0 | 0.3635 | 0.3046 | 0.3251 | 6998.94 | 5.37 | 96.23 | 79.6 | 98.47 | 97.79 | 295.57 | 237.188 | 277.578 | 0.929 |
| 0.6866 | 0.1988 | 0.0248 | 0.2795 | 0.3115 | 0.3328 | 6538.01 | 5.73 | 95.13 | 73.83 | 96.64 | 98.00 | 301.16 | 228.878 | 266.696 | 0.878 |
| 0.8449 | 0.2342 | 0.0953 | 0.2892 | 0.3215 | 0.3414 | 5995.08 | 5.22 | 91.53 | 59.29 | 92.74 | 97.25 | 309.31 | 218.155 | 252.175 | 0.808 |
| 0.6349 | 0.2504 | 0.0792 | 0.2601 | 0.3313 | 0.351 | 5548.5 | 5.54 | 93.91 | 68.94 | 90.65 | 97.40 | 313.3 | 210.064 | 240.715 | 0.761 |
| 0.9128 | 0.4152 | 0.2246 | 0.3118 | 0.3469 | 0.364 | 4975.03 | 5.43 | 90.38 | 56.03 | 85.31 | 97.59 | 323.77 | 194.652 | 217.693 | 0.667 |
| 0.5089 | 0.3603 | 0.1696 | 0.2052 | 0.3646 | 0.3783 | 4463.73 | 5.73 | 92.33 | 64.22 | 79.59 | 97.14 | 330.6 | 181.285 | 196.789 | 0.590 |
| 0.8901 | 0.8934 | 0.3506 | 0.2924 | 0.3807 | 0.3771 | 3995.76 | 0.1 | 94.38 | 78.92 | 80.98 | 106.26 | 329.1 | 171.982 | 182.288 | 0.549 |
| 0.7286 | 1 | 0.4701 | 0.0792 | 0.4053 | 0.3854 | 3455.83 | -2.32 | 90.87 | 69.36 | 74.95 | 114.35 | 336.56 | 154.157 | 152.908 | 0.451 |
| 0.3086 | 0.6606 | 0.2504 | 0.01 | 0.428 | 0.3881 | 3021.1 | -5.27 | 92.3 | 75.42 | 71.38 | 127.84 | 335.64 | 141.502 | 133.013 | 0.394 |
| 0.1696 | 0.6381 | 0.189 | 0.01 | 0.4527 | 0.3953 | 2679.95 | -5.16 | 92.92 | 79.71 | 62.74 | 134.56 | 335.37 | 129.014 | 113.417 | 0.336 |
| 0.1309 | 0.748 | 0.1826 | 0.01 | 0.4701 | 0.3966 | 2456.11 | -5.76 | 91.69 | 81.28 | 57.59 | 144.40 | 332.59 | 120.744 | 101.327 | 0.303 |
| 0.0889 | 0.9677 | 0.2019 | 0 | 0.4921 | 0.4001 | 2231.92 | -4.93 | 90.16 | 78.05 | 48.64 | 152.91 | 331.08 | 109.351 | 84.199 | 0.253 |
| 0 | 1 | 0.1373 | 0 | 0.5307 | 0.3979 | 1874.46 | -4.24 | 85.35 | 69.76 | 35.92 | | 321.41 | | | |

FIG. 13B

| Blue Channel Relative Intensity | Red Channel Relative Intensity | Yellow-Green Channel Relative Intensity | Cyan Channel OFF | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 0.7868 | 0.0921 | 0.3376 | | 0.3464 | 0.3637 | 4992.27 | 5.49 | 74.13 | -7.14 | 79.02 | 93.92 | 336.16 | 187.743 | 206.189 | 0.608 |
| 0.7868 | 0.2181 | 0.3958 | | 0.3612 | 0.3734 | 4542.06 | 4.65 | 76.89 | 9.43 | 77.13 | 96.56 | 340.28 | 177.236 | 189.128 | 0.550 |
| 0.7027 | 0.4313 | 0.3764 | | 0.3785 | 0.3742 | 4034.42 | -0.6 | 82.99 | 41.19 | 79.66 | 106.82 | 336.86 | 168.181 | 175.007 | 0.515 |
| 0.4992 | 0.5508 | 0.3312 | | 0.4007 | 0.3836 | 3545.23 | -2.12 | 86.93 | 57.09 | 75.58 | 113.22 | 338.91 | 155.346 | 154.237 | 0.451 |
| 0.2601 | 0.5897 | 0.2213 | | 0.4315 | 0.3888 | 2965.23 | -5.47 | 92.18 | 74.86 | 71.05 | 128.97 | 335.92 | 140.426 | 131.214 | 0.388 |
| 0.2246 | 0.7286 | 0.2375 | | 0.4474 | 0.3943 | 2751.55 | -5.07 | 92.78 | 76.95 | 64.60 | 133.56 | 336.51 | 131.032 | 116.230 | 0.343 |
| 0.1535 | 0.8288 | 0.2149 | | 0.4687 | 0.397 | 2475.82 | -5.55 | 92.15 | 79.29 | 57.90 | 144.01 | 333.84 | 120.708 | 100.788 | 0.300 |
| 0.0565 | 1 | 0.1792 | | 0.5057 | 0.3985 | 2087.13 | -5.26 | 88.42 | 75.85 | 44.48 | 166.45 | 327.24 | 102.823 | 75.777 | 0.231 |
| 0 | 1 | 0.1242 | | 0.5347 | 0.3916 | 1807.61 | -5.75 | 84.21 | 66.75 | 35.92 | 212.05 | 316.73 | 89.110 | 60.023 | 0.189 |

FIG. 13C

| Blue Channel Relative Intensity | Red Channel Relative Intensity | Yellow-Green Channel OFF | Cyan Channel Relative Intensity | ccx | ccy | CCT | duv | Ra | R9 | GAI | GAIBB | LER (Luminous efficacy of radiation) (lm/W) | melotonian suppressing mW per 100 lumens | CER (Circadian efficacy of radiation) (blm/W) | CAF (Circadian action factor) (blm/lm) |
|---|---|---|---|---|---|---|---|---|---|---|---|---|---|---|---|
| 1 | 0.05 | | 0.2569 | 0.2783 | 0.2965 | 9804.25 | 5.73 | 87.11 | 34.54 | | | 281.95 | | | |
| 1 | 0.1147 | | 0.3053 | 0.2874 | 0.3066 | 8561.51 | 5.44 | 90.77 | 53.75 | | | 286.89 | | | |
| 1 | 0.1502 | | 0.3376 | 0.2922 | 0.3126 | 8027.91 | 5.79 | 92.34 | 60.8 | 98.43 | 95.90 | 289.87 | 249.109 | 292.808 | 0.998 |
| 0.8966 | 0.2246 | | 0.3764 | 0.3037 | 0.3261 | 7038.68 | 6.38 | 95.82 | 76.07 | 97.74 | 97.11 | 296.2 | 237.335 | 277.915 | 0.928 |
| 0.8449 | 0.2924 | | 0.399 | 0.3124 | 0.3334 | 6484.24 | 5.59 | 97.78 | 89.05 | 97.77 | 98.59 | 299.15 | 229.825 | 267.870 | 0.887 |
| 0.6898 | 0.3118 | | 0.3764 | 0.3211 | 0.3423 | 6012.52 | 5.89 | 97.29 | 96.23 | 96.08 | 98.71 | 302.96 | 222.454 | 257.960 | 0.844 |
| 0.9128 | 0.5315 | | 0.5703 | 0.33 | 0.3505 | 5602.88 | 5.84 | 95.39 | 93.79 | 94.34 | 99.01 | 306.19 | 215.280 | 248.012 | 0.803 |
| 0.7027 | 0.6349 | | 0.5703 | 0.3471 | 0.3653 | 4970.86 | 5.95 | 91.55 | 82.17 | 89.61 | 98.59 | 311.76 | 202.573 | 229.882 | 0.732 |
| 0.2536 | 0.3376 | | 0.2601 | 0.3634 | 0.3769 | 4491.61 | 5.49 | 87.44 | 70.9 | 84.62 | 98.13 | 315.53 | 191.775 | 213.984 | 0.674 |
| 0.5089 | 0.9354 | | 0.5638 | 0.3797 | 0.3774 | 4026.34 | 0.57 | 82.24 | 55.79 | 84.48 | 104.97 | 313.55 | 182.904 | 200.851 | 0.637 |
| 0.2052 | 0.5994 | | 0.2892 | 0.4024 | 0.3839 | 3508.05 | -2.38 | 76.95 | 47.71 | 78.93 | 110.51 | 313.7 | 170.053 | 181.853 | 0.577 |
| 0.1567 | 0.8352 | | 0.3118 | 0.431 | 0.389 | 2975.14 | -5.32 | 71.62 | 46.67 | 70.69 | 120.33 | 312.4 | 154.608 | 159.291 | 0.508 |

FIG 13D

| | Blue, Red, and Cyan Channels | | | Blue, Red, and Yellow/Green Channels | | | Comparison of Emitting Modes | |
|---|---|---|---|---|---|---|---|---|
| CCT approx. | CCT | duv | Circadian Action Factor (CAF) | CCT | duv | Circadian Action Factor (CAF) | delta u'v' [pts] | Increase in Circadian Action Factor (CAF) |
| 5000 | 4970.86 | 5.95 | 0.732 | 4992.27 | 5.49 | 0.608 | 0.84 | 20.5% |
| 4500 | 4491.61 | 5.49 | 0.674 | 4542.06 | 4.65 | 0.550 | 1.86 | 22.5% |
| 4000 | 4026.34 | 0.57 | 0.637 | 4034.42 | -0.6 | 0.515 | 1.67 | 23.7% |
| 3500 | 3508.05 | -2.38 | 0.577 | 3545.23 | -2.12 | 0.451 | 1.09 | 27.8% |
| 3000 | 2975.14 | -5.32 | 0.508 | 2965.23 | -5.47 | 0.388 | 0.40 | 30.9% |

FIG. 14

| Part Number | Bin | Dominant/Peak wavelength (nm) | |
|---|---|---|---|
| | | Minimum | Maximum |
| LXZ1-PB01 | 1 | 460 | 465 |
| | 2 | 465 | 470 |
| | 5 | 480 | 485 |
| LXZ1-PR01 | 3 | 440 | 445 |
| | 4 | 445 | 450 |
| | 5 | 450 | 455 |
| | 6 | 455 | 460 |
| LXZ1-PE01 | 1 | 490 | 498 |
| | 2 | 498 | 508 |
| | 6 | 490 | 495 |
| | 7 | 495 | 500 |
| | 8 | 500 | 505 |
| | 9 | 505 | 510 |

METHODS FOR GENERATING MELATONIN-RESPONSE-TUNED WHITE LIGHT WITH HIGH COLOR RENDERING

FIELD OF THE DISCLOSURE

This disclosure is in the field of solid-state lighting. In particular, the disclosure relates to methods of providing white light with tunable color temperature and circadian energy performance.

BACKGROUND

A wide variety of light emitting devices are known in the art including, for example, incandescent light bulbs, fluorescent lights, and semiconductor light emitting devices such as light emitting diodes ("LEDs").

There are a variety of resources utilized to describe the light produced from a light emitting device, one commonly used resource is 1931 CIE (Commission Internationale de l'Éclairage) Chromaticity Diagram. The 1931 CIE Chromaticity Diagram maps out the human color perception in terms of two CIE parameters x and y. The spectral colors are distributed around the edge of the outlined space, which includes all of the hues perceived by the human eye. The boundary line represents maximum saturation for the spectral colors, and the interior portion represents less saturated colors including white light. The diagram also depicts the Planckian locus, also referred to as the black body locus (BBL), with correlated color temperatures, which represents the chromaticity coordinates (i.e., color points) that correspond to radiation from a black-body at different temperatures. Illuminants that produce light on or near the BBL can thus be described in terms of their correlated color temperatures (CCT). These illuminants yield pleasing "white light" to human observers, with general illumination typically utilizing CCT values between 1,800K and 10,000K.

Color rendering index (CRI) is described as an indication of the vibrancy of the color of light being produced by a light source. In practical terms, the CRI is a relative measure of the shift in surface color of an object when lit by a particular lamp as compared to a reference light source, typically either a black-body radiator or the daylight spectrum. The higher the CRI value for a particular light source, the better that the light source renders the colors of various objects it is used to illuminate. LEDs have the potential to exhibit very high power efficiencies relative to conventional incandescent or fluorescent lights. Most LEDs are substantially monochromatic light sources that appear to emit light having a single color. Thus, the spectral power distribution of the light emitted by most LEDs is tightly centered about a "peak" wavelength, which is the single wavelength where the spectral power distribution or "emission spectrum" of the LED reaches its maximum as detected by a photo-detector. LEDs typically have a full-width half-maximum wavelength range of about 10 nm to 30 nm, comparatively narrow with respect to the broad range of visible light to the human eye, which ranges from approximately from 380 nm to 800 nm.

In order to use LEDs to generate white light, LED lamps have been provided that include two or more LEDs that each emit a light of a different color. The different colors combine to produce a desired intensity and/or color of white light. For example, by simultaneously energizing red, green and blue LEDs, the resulting combined light may appear white, or nearly white, depending on, for example, the relative intensities, peak wavelengths and spectral power distributions of the source red, green and blue LEDs. The aggregate emissions from red, green, and blue LEDs typically provide poor CRI for general illumination applications due to the gaps in the spectral power distribution in regions remote from the peak wavelengths of the LEDs.

White light may also be produced by utilizing one or more luminescent materials such as phosphors to convert some of the light emitted by one or more LEDs to light of one or more other colors. The combination of the light emitted by the LEDs that is not converted by the luminescent material(s) and the light of other colors that are emitted by the luminescent material(s) may produce a white or near-white light.

LED lamps have been provided that can emit white light with different CCT values within a range. Such lamps utilize two or more LEDs, with or without luminescent materials, with respective drive currents that are increased or decreased to increase or decrease the amount of light emitted by each LED. By controllably altering the power to the various LEDs in the lamp, the overall light emitted can be tuned to different CCT values. The range of CCT values that can be provided with adequate CRI values and efficiency is limited by the selection of LEDs.

The spectral profiles of light emitted by white artificial lighting can impact circadian physiology, alertness, and cognitive performance levels. Bright artificial light can be used in a number of therapeutic applications, such as in the treatment of seasonal affective disorder (SAD), certain sleep problems, depression, jet lag, sleep disturbances in those with Parkinson's disease, the health consequences associated with shift work, and the resetting of the human circadian clock. Artificial lighting may change natural processes, interfere with melatonin production, or disrupt the circadian rhythm. Blue light may have a greater tendency than other colored light to affect living organisms through the disruption of their biological processes which can rely upon natural cycles of daylight and darkness. Exposure to blue light late in the evening and at night may be detrimental to one's health.

Significant challenges remain in providing LED lamps that can provide white light across a range of CCT values while simultaneously achieving high efficiencies, high luminous flux, good color rendering, and acceptable color stability. It is also a challenge to provide lighting apparatuses that can provide desirable lighting performance while allowing for the control of circadian energy performance.

DISCLOSURE

The present disclosure provides aspects of methods of generating white light with tunable circadian energy performance. The methods can comprise producing light from the blue, red, yellow/green, and cyan channels described herein, in various combinations of two or more of the channels at any given time. The methods comprise producing light from a first light emitting diode ("LED") string, producing light from a second LED string, producing light from a third LED string, a fourth LED string, or both the third LED string and the fourth LED string, passing the light produced by each of the first, second, third, and fourth LED strings through one of a plurality of respective luminophoric mediums, combining the light exiting the plurality of respective luminophoric mediums together into white light, wherein the combined white light corresponds to at least one of a plurality of points along a predefined path near the black body locus in the 1931 CIE Chromaticity Diagram, wherein the first, second, and third LED strings comprise a blue LED having a peak wavelength of about 405 nm and about 485 nm and the fourth LED string comprises a cyan LED having a peak wavelength of between about 485 nm and about 520 nm. In some implementations, substantially the same white light, in terms of position on the 1931 CIE chromaticity diagram, can be generated in two or more light emitting modes. White light can be generated within a 7-step MacAdam ellipse of a plurality of target CCTs selected from between 1800K and 4200K via a plurality of emitting modes, the emitting modes comprising a first emitting mode, wherein the method comprises producing light from the first, second, third, and fourth LED strings; a second emitting mode, wherein the method comprises producing light from the first, second, and third LED strings but not the fourth LED string; and a third emitting mode, wherein the method comprises producing light from the first, second, and fourth LED strings but not the third LED string. For a particular target CCT, the white light generated in two of the light emitting modes can be within about 0.1, about 0.2, about 0.3, about 0.4, about 0.5, about 0.6, about 0.7, about 0.8, about 0.9, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, or between about 8.0 and about 10.0 standard deviations of color matching (SDCM). In preferred embodiments, the white light generated in two of the light emitting modes at a target CCT is within about 0.1 to about 3.0 SDCM. In further preferred embodiments, the white light generated in two of the light emitting modes at a target CCT is within about 0.1 to about 1.0 SDCM, or more preferably within about 0.1 to about 0.5 SDCM. For each target CCT, the respective circadian action factor values of the white light generated in any two of the first, second, and third emitting modes differ from each other by a predetermined threshold amount. The predetermined threshold amount may be at least about 5%, 10%, 15%, 20% 25%, 30%, 35%, 40%, 50%, 60%, 70%, 80%, 100%, 125%, 150%, 200%, 300%, 400%, or more. In some implementations, the circadian energy tuning can be achieved between emitting modes while generating white light corresponding to a plurality of points along a predefined path within 7-step MacAdam ellipse of the Planckian locus with the light generated at each point having one or more of Ra≥80, R9≥50, and GAIBB≥90.

The general disclosure and the following further disclosure are exemplary and explanatory only and are not restrictive of the disclosure, as defined in the appended claims. Other aspects of the present disclosure will be apparent to those skilled in the art in view of the details as provided herein. In the figures, like reference numerals designate corresponding parts throughout the different views. All callouts and annotations are hereby incorporated by this reference as if fully set forth herein.

DRAWINGS

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale. In the drawings:

FIGS. 7-8 are tables of data of relative spectral power versus wavelength regions for some suitable color points of light generated by components of devices of the present disclosure;

FIGS. 9A-9D are tables of data of color rendering characteristics of an implementation of the present disclosure;

FIG. 10A-10D are tables of data of color rendering characteristics of an implementation of the present disclosure;

FIG. 11A-11D are tables of data of color rendering characteristics of an implementation of the present disclosure;

FIG. 12A-12D are tables of data of color rendering characteristics of an implementation of the present disclosure;

FIG. 13A-13D are tables of data of color rendering characteristics of an implementation of the present disclosure; and FIG. 14 a table of data of light output of light emitting diodes suitable for implementations of the present disclosure.

All descriptions and callouts in the Figures are hereby incorporated by this reference as if fully set forth herein.

FURTHER DISCLOSURE

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular exemplars by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another exemplar includes from the one particular value and/or to the other particular value. Similarly, when values are expressed as approximations, by use of the antecedent "about," it will be understood that the particular value forms another exemplar. All ranges are inclusive and combinable.

It is to be appreciated that certain features of the disclosure which are, for clarity, described herein in the context of separate exemplar, may also be provided in combination in a single exemplary implementation. Conversely, various features of the disclosure that are, for brevity, described in the context of a single exemplary implementation, may also be provided separately or in any subcombination. Further, reference to values stated in ranges include each and every value within that range.

Figure 1:
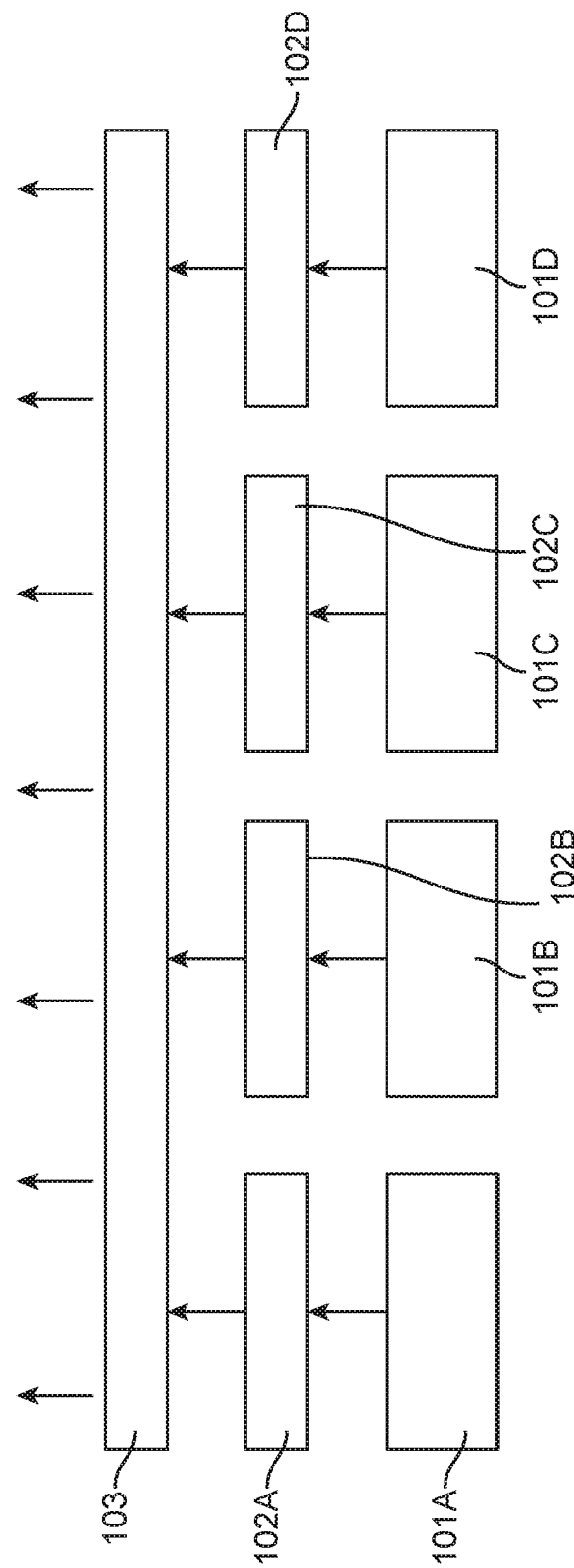
FIG. 1 illustrates aspects of light emitting devices according to the present disclosure.

In one aspect, the present disclosure provides semiconductor light emitting devices 100 that can have a plurality of light emitting diode (LED) strings. Each LED string can have one, or more than one, LED. As depicted schematically in FIG. 1, the device 100 may comprise one or more LED strings (101A/101B/101C/101D) that emit light (schematically shown with arrows). In some instances, the LED strings can have recipient luminophoric mediums (102A/102B/102C/102D) associated therewith. The light emitted from the LED strings, combined with light emitted from the recipient luminophoric mediums, can be passed through one or more optical elements 103. Optical elements 103 may be one or more diffusers, lenses, light guides, reflective elements, or combinations thereof.

A recipient luminophoric medium 102A, 102B, 102C, or 102D includes one or more luminescent materials and is positioned to receive light that is emitted by an LED or other semiconductor light emitting device. In some implementations, recipient luminophoric mediums include layers having luminescent materials that are coated or sprayed directly onto a semiconductor light emitting device or on surfaces of the packaging thereof, and clear encapsulants that include luminescent materials that are arranged to partially or fully cover a semiconductor light emitting device. A recipient luminophoric medium may include one medium layer or the like in which one or more luminescent materials are mixed, multiple stacked layers or mediums, each of which may include one or more of the same or different luminescent materials, and/or multiple spaced apart layers or mediums, each of which may include the same or different luminescent materials. Suitable encapsulants are known by those skilled in the art and have suitable optical, mechanical, chemical, and thermal characteristics. In some implementations, encapsulants can include dimethyl silicone, phenyl silicone, epoxies, acrylics, and polycarbonates. In some implementations, a recipient luminophoric medium can be spatially separated (i.e., remotely located) from an LED or surfaces of the packaging thereof. In some implementations, such spatial segregation may involve separation of a distance of at least about 1 mm, at least about 2 mm, at least about 5 mm, or at least about 10 mm. In certain embodiments, conductive thermal communication between a spatially segregated luminophoric medium and one or more electrically activated emitters is not substantial. Luminescent materials can include phosphors, scintillators, day glow tapes, nanophosphors, inks that glow in visible spectrum upon illumination with light, semiconductor quantum dots, or combinations thereof. In some implementations, the luminescent materials may comprise phosphors comprising one or more of the following materials: $BaMg_2Al_{16}O_{27}:Eu^{2+}$, $BaMg_2Al_{16}O_{27}:Eu^{2+},Mn^{2+}$, $CaSiO_3:Pb,Mn$, $CaWO_4:Pb$, $MgWO_4$, $Sr_5Cl(PO_4)_3:Eu^{2+}$, $Sr_2P_2O_7:Sn^{2+}$, $Sr_6P_5BO_{20}:Eu$, $Ca_5F(PO_4)_3:Sb$, $(Ba,Ti)_2P_2O_7:Ti$, $Sr_5F(PO_4)_3:Sb,Mn$, $(La,Ce,Tb)PO_4:Ce,Tb$, $(Ca,Zn,Mg)_3(PO_4)_2:Sn$, $(Sr,Mg)_3(PO_4)_2:Sn$, $Y_2O_3:Eu^{3+}$, $Mg_4(F)GeO_6:Mn$, $LaMgAl_{11}O_{19}:Ce$, $LaPO_4:Ce$, $SrAl_{12}O_{19}:Ce$, $BaSi_2O_5:Pb$, $SrB_4O_7:Eu$, $Sr_2MgSi_2O_7:Pb$, $Gd_2O_2S:Tb$, $Gd_2O_2S:Eu$, $Gd_2O_2S:Pr$, $Gd_2O_2S:Pr,Ce,F$, $Y_2O_2S:Tb$, $Y_2O_2S:Eu$, $Y_2O_2S:Pr$, $Zn(0.5)Cd(0.4)S:Ag$, $Zn(0.4)Cd(0.6)S:Ag$, $Y_2SiO_5:Ce$, $YAlO_3:Ce$, $Y_3(Al,Ga)_5O_{12}:Ce$, $CdS:In$, $ZnO:Ga$, $ZnO:Zn$, $(Zn,Cd)S:Cu,Al$, $ZnCdS:Ag,Cu$, $ZnS:Ag$, $ZnS:Cu$, $NaI$, $CsI:Tl$, $^6LiF/ZnS:Ag$, $^6LiF/ZnS:Cu,Al,Au$, $ZnS:Cu,Al$, $ZnS:Cu,Au,Al$, $CaAlSiN_3:Eu$, $(Sr,Ca)AlSiN_3:Eu$, $(Ba,Ca,Sr,Mg)_2SiO_4:Eu$, $Lu_3Al_5O_{12}:Ce$, $Eu^{3+}(Gd_{0.9}Y_{0.1})_3Al_5O_{12}:Bi^{3+},Tb^{3+}$, $Y_3Al_5O_{12}:Ce$, $(La,Y)_3Si_6N_{11}:Ce$, $Ca_2AlSi_3O_2N_5:Ce^{3+}$, $Ca_2AlSi_3O_2N_5:Eu^{2+}$, $BaMgAl_{10}O_{17}:Eu$, $Sr_5(PO_4)_3C_1:Eu$, $(Ba,Ca,Sr,Mg)_2SiO_4:Eu$, $Si_{6-z}Al_zN_{8-z}O_z:Eu$ (wherein $0<z\leq4.2$); $M_3Si_6O_{12}N_2:Eu$ (wherein M=alkaline earth metal element), $(Mg,Ca,Sr,Ba)Si_2O_2N_2:Eu$, $Sr_4Al_{14}O_{25}:Eu$, $(Ba,Sr,Ca)Al_2O_4:Eu$, $(Sr,Ba)Al_2Si_2O_8:Eu$, $(Ba,Mg)_2SiO_4:Eu$, $(Ba,Sr,Ca)_2(Mg,Zn)Si_2O_7:Eu$, $(Ba,Ca,Sr,Mg)_9(Sc,Y,Lu,Gd)_2(Si,Ge)_6O_{24}:Eu$, $Y_2SiO_5:CeTb$, $Sr_2P_2O_7—Sr_2B_2O_5:Eu$, $Sr_2Si_3O_8\cdot2SrCl_2:Eu$, $Zn_2SiO_4:Mn$, $CeMgAl_{11}O_{19}:Tb$, $Y_3Al_5O_{12}:Tb$, $Ca_2Y_8(SiO_4)_6O_2:Tb$, $La_3Ga_5SiO_{14}:Tb$, $(Sr,Ba,Ca)Ga_2S_4:Eu,Tb,Sm$, $Y_3(Al,Ga)_5O_{12}:Ce$, $(Y,Ga,Tb,La,Sm,Pr,Lu)_3(Al,Ga)_5O_{12}:Ce$, $Ca_3Sc_2Si_3O_{12}:Ce$, $Ca_3(Sc,Mg,Na,Li)_2Si_3O_{12}:Ce$, $CaSc_2O_4:Ce$, Eu-activated β-Sialon, $SrAl_2O_4:Eu$, $(La,Gd,Y)_2O_2S:Tb$, $CeLaPO_4:Tb$, $ZnS:Cu,Al$, $ZnS:Cu,Au,Al$, $(Y,Ga,Lu,Sc,La)BO_3:Ce,Tb$, $Na_2Gd_2B_2O_7:Ce,Tb$, $(Ba,Sr)_2(Ca,Mg,Zn)B_2O_6:K,Ce,Tb$, $Ca_8Mg(SiO_4)_4Cl_2:Eu,Mn$, $(Sr,Ca,Ba)(Al,Ga,In)_2S_4:Eu$, $(Ca,Sr)_8(Mg,Zn)(SiO_4)_4Cl_2:Eu,Mn$, $M_3Si_6O_9N_4:Eu$, $Sr_5Al_5Si_{21}O_2N_{35}:Eu$, $Sr_3Si_{13}Al_3N_{21}O_2:Eu$, $(Mg,Ca,Sr,Ba)_2Si_5N_8:Eu$, $(La,Y)_2O_2S:Eu$, $(Y,La,Gd,Lu)_2O_2S:Eu$, $Y(V,P)O_4:Eu$, $(Ba,Mg)_2SiO_4:Eu,Mn$, $(Ba,Sr,Ca,Mg)_2SiO_4:Eu,Mn$, $LiW_2O_8:Eu$, $LiW_2O_8:Eu,Sm$, $Eu_2W_2O_9$, $Eu_2W_2O_9:Nb$ and $Eu_2W_2O_9:Sm$, $(Ca,Sr)S:Eu$, $YAlO_3:Eu$, $Ca_2Y_8(SiO_4)_6O_2:Eu$, $LiY_9(SiO_4)_6O_2:Eu$, $(Y,Gd)_3Al_5O_{12}:Ce$, $(Tb,Gd)_3Al_5O_{12}:Ce$, $(Mg,Ca,Sr,Ba)_2Si_5(N,O)_8:Eu$, $(Mg,Ca,Sr,Ba)Si(N,O)_2:Eu$, $(Mg,Ca,Sr,Ba)AlSi(N,O)_3:Eu$, $(Sr,Ca,Ba,Mg)_{10}(PO_4)_6Cl_2:Eu, Mn$, $Eu,Ba_3MgSi_2O_8:Eu,Mn$, $(Ba,Sr,Ca,Mg)_3(Zn,Mg)Si_2O_8:Eu,Mn$, $(k-x)MgO\cdot xAF_2\cdot GeO_2:yMn^{4+}$ (wherein k=2.8 to 5, x=0.1 to 0.7, y=0.005 to 0.015, A=Ca, Sr, Ba, Zn or a mixture thereof), Eu-activated α-Sialon, $(Gd,Y,Lu,La)_2O_3:Eu, Bi$, $(Gd,Y,Lu,La)_2O_2S:Eu,Bi$, $(Gd,Y,Lu,La)VO_4:Eu,Bi$, $SrY_2S_4:Eu,Ce$, $CaLa_2S_4:Ce,Eu$, $(Ba,Sr,Ca)MgP_2O_7:Eu,Mn$, $(Sr,Ca,Ba,Mg,Zn)_2P_2O_7:Eu,Mn$, $(Y,Lu)_2WO_6:Eu,Ma$, $(Ba,Sr,Ca)_xSi_yN_z:Eu,Ce$ (wherein x, y and z are integers equal to or greater than 1), $(Ca,Sr,Ba,Mg)_{10}(PO_4)_6(F,Cl,Br,OH):Eu,Mn$, $((Y,Lu,Gd,Tb)_{1-x-y}Sc_xCe_y)_2(Ca,Mg)(Mg,Zn)_{2+r}Si_{z-q}Ge_qO_{12+\delta}$, $SrAlSi_4N_{b\ 7}$, $Sr_2Al_2Si_9O_2N_{14}:Eu$, $M^1_aM^2_bM^3_cO_d$ (wherein $M^1$=activator element including at least Ce, $M^2$=bivalent metal element, $M^3$=trivalent metal element, $0.0001\leq a\leq0.2$, $0.8\leq b\leq1.2$, $1.6\leq c\leq2.4$ and $3.2\leq d\leq4.8$), $A_{2+x}M_yMn_zF_n$ (wherein A=Na and/or K; M=Si and Al, and $-1\leq x\leq1$, $0.9\leq y+z\leq1.1$, $0.001\leq z\leq0.4$ and $5\leq n\leq7$), KSF/KSNAF, or $(La_{1-x-y}, Eu_x, Ln_y)_2O_2S$ (wherein $0.02\leq x\leq0.50$ and $0\leq y\leq0.50$, Ln=$Y^{3+}$, $Gd^{3+}$, $Lu^{3+}$, $Sc^{3+}$, $Sm^{3+}$or $Er^{3+}$). In some preferred implementations, the luminescent materials may comprise phosphors comprising one or more of the following materials: $CaAlSiN_3:Eu$, $(Sr,Ca)AlSiN_3:Eu$, $BaMgAl_{10}O_{17}:Eu$, $(Ba,Ca,Sr,Mg)_2SiO_4:Eu$, β-SiAlON, $Lu_3Al_5O_{12}:Ce$, $EU^{3+}(Cd_{0.9}Y_{0.1})_3Al_5O_{12}:Bi^{3+}$, $Tb^{3+}$, $Y_3Al_5O_{12}:Ce$, $La_3Si_6N_{11}:Ce$, $(La,Y)_3Si_6N_{11}:Ce$, $Ca_2AlSi_3O_2N_5:Ce^{3+}$, $Ca_2AlSi_3O_2N_5:Ce^{3+},Eu^{2+}$, $Ca_2AlSi_3O_2N_5:Eu^{2+}$, $BaMgAl_{10}O_{17}:Eu^{2+}$, $Sr_{4.5}Eu_{0.5}(PO_4)_3Cl$, or $M^1_aM^2_bM^3_cO_d$ (wherein $M^1$=activator element comprising Ce, $M^2$=bivalent metal element, $M^3$=trivalent metal element, $0.0001\leq a\leq0.2$, $0.8\leq b\leq1.2$, $1.6\leq c\leq2.4$ and $3.2\leq d\leq4.8$). In further preferred implementations, the luminescent materials may comprise phosphors comprising one or more of the following materials: $CaAlSiN_3:Eu$, $BaMgAl_{10}O_{17}:Eu$, $Lu_3Al_5O_{12}:Ce$, or $Y_3Al_5O_{12}:Ce$.

Figure 2:
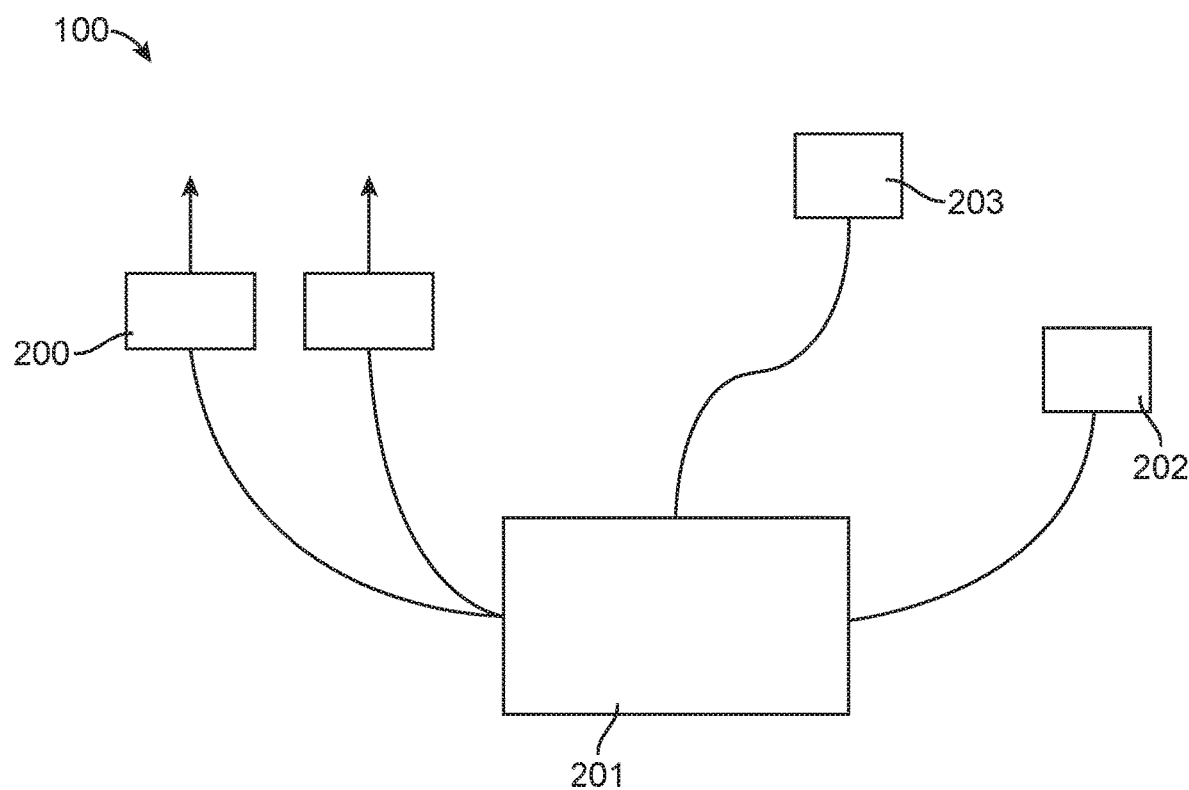
FIG. 2 illustrates aspects of light emitting devices according to the present disclosure.

Some implementations of the present invention relate to use of solid state emitter packages. A solid state emitter package typically includes at least one solid state emitter chip that is enclosed with packaging elements to provide environmental and/or mechanical protection, color selection, and light focusing, as well as electrical leads, contacts or traces enabling electrical connection to an external circuit. Encapsulant material, optionally including luminophoric material, may be disposed over solid state emitters in a solid state emitter package. Multiple solid state emitters may be provided in a single package. A package including multiple solid state emitters may include at least one of the following: a single leadframe arranged to conduct power to the solid state emitters, a single reflector arranged to reflect at least a portion of light emanating from each solid state emitter, a single submount supporting each solid state emitter, and a single lens arranged to transmit at least a portion of light emanating from each solid state emitter. Individual LEDs or groups of LEDs in a solid state package (e.g., wired in series) may be separately controlled. As depicted schematically in FIG. 2, multiple solid state packages 200 may be arranged in a single semiconductor light emitting device 100. Individual solid state emitter packages or groups of solid state emitter packages (e.g., wired in series) may be separately controlled. Separate control of individual emitters, groups of emitters, individual packages, or groups of packages, may be provided by independently applying drive currents to the relevant components with control elements known to those skilled in the art. In one embodiment, at least one control circuit 201a may include a current supply circuit configured to independently apply an on-state drive current to each individual solid state emitter, group of solid state emitters, individual solid state emitter package, or group of solid state emitter packages. Such control may be responsive to a control signal (optionally including at least one sensor 202 arranged to sense electrical, optical, and/or thermal properties and/or environmental conditions), and a control system 203 may be configured to selectively provide one or more control signals to the at least one current supply circuit. In various embodiments, current to different circuits or circuit portions may be pre-set, user-defined, or responsive to one or more inputs or other control parameters. The design and fabrication of semiconductor light emitting devices are well known to those skilled in the art, and hence further description thereof will be omitted. Unless otherwise defined, terms used herein should be construed to have the same meaning as commonly understood by one of ordinary skill in the art to which this invention belongs. It will be further understood that terms used herein should be interpreted as having a meaning that is consistent with their meaning in the context of this specification and the relevant art, and should not be interpreted in an idealized or overly formal sense unless expressly so defined herein.

Figure 3:
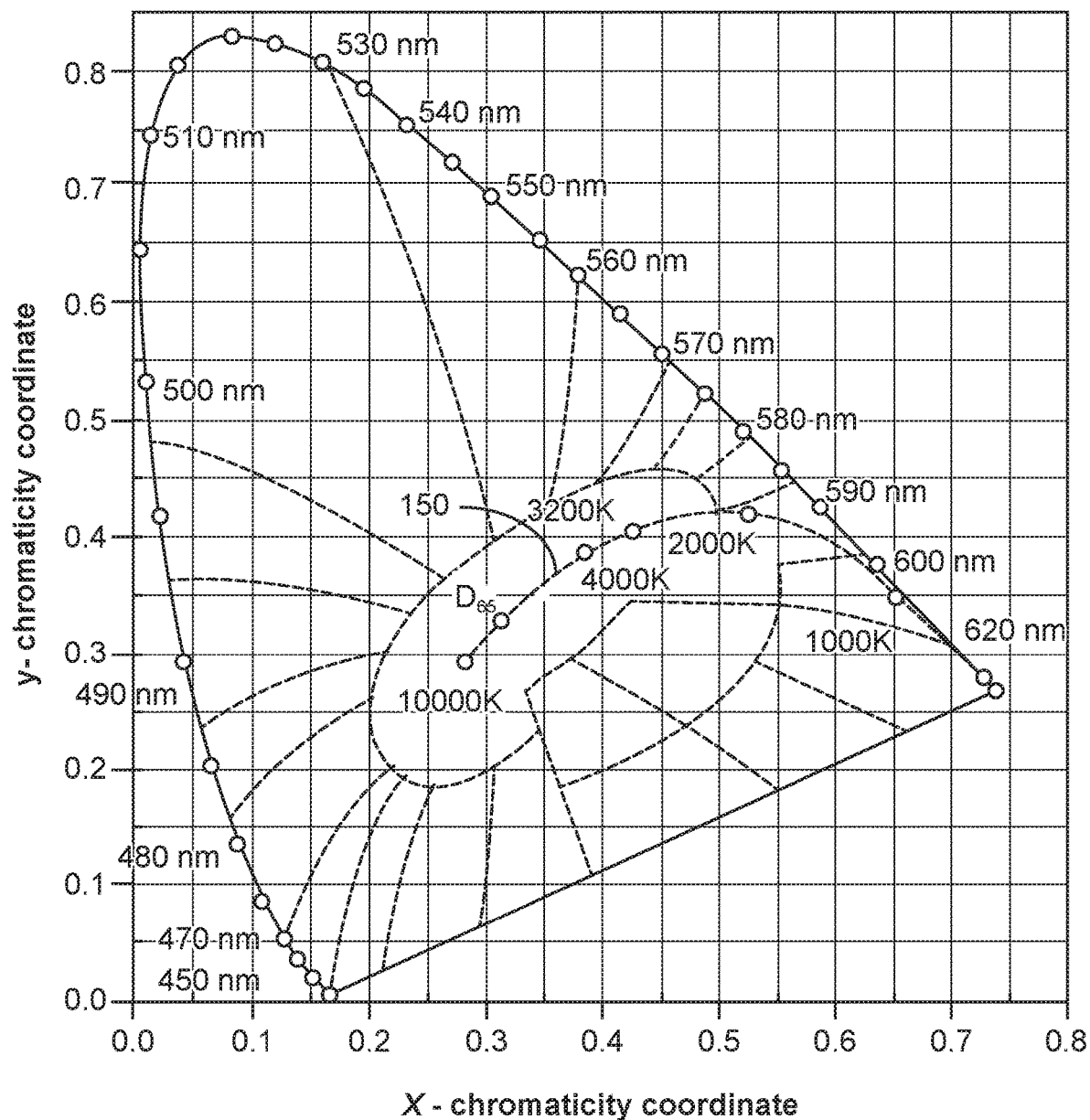
FIG. 3 depicts a graph of a 1931 CIE Chromaticity Diagram illustrating the location of the Planckian locus.

FIG. 3 illustrates a 1931 International Commission on Illumination (CIE) chromaticity diagram. The 1931 CIE Chromaticity diagram is a two-dimensional chromaticity space in which every visible color is represented by a point having x- and y-coordinates. Fully saturated (monochromatic) colors appear on the outer edge of the diagram, while less saturated colors (which represent a combination of wavelengths) appear on the interior of the diagram. The term "saturated", as used herein, means having a purity of at least 85%, the term "purity" having a well-known meaning to persons skilled in the art, and procedures for calculating purity being well-known to those of skill in the art. The Planckian locus, or black body locus (BBL), represented by line 150 on the diagram, follows the color an incandescent black body would take in the chromaticity space as the temperature of the black body changes from about 1000K to 10,000 K. The black body locus goes from deep red at low temperatures (about 1000 K) through orange, yellowish white, white, and finally bluish white at very high temperatures. The temperature of a black body radiator corresponding to a particular color in a chromaticity space is referred to as the "correlated color temperature." In general, light corresponding to a correlated color temperature (CCT) of about 2700 K to about 6500 K is considered to be "white" light. In particular, as used herein, "white light" generally refers to light having a chromaticity point that is within a 10-step MacAdam ellipse of a point on the black body locus having a CCT between 2700K and 6500K. However, it will be understood that tighter or looser definitions of white light can be used if desired. For example, white light can refer to light having a chromaticity point that is within a seven step MacAdam ellipse of a point on the black body locus having a CCT between 2700K and 6500K. The distance from the black body locus can be measured in the CIE 1960 chromaticity diagram, and is indicated by the symbol Auv, or DUV. If the chromaticity point is above the Planckian locus the DUV is denoted by a positive number; if the chromaticity point is below the locus, DUV is indicated with a negative number. If the DUV is sufficiently positive, the light source may appear greenish or yellowish at the same CCT. If the DUV is sufficiently negative, the light source can appear to be purple or pinkish at the same CCT. Observers may prefer light above or below the Planckian locus for particular CCT values. DUV calculation methods are well known by those of ordinary skill in the art and are more fully described in ANSI C78.377, American National Standard for Electric Lamps—Specifications for the Chromaticity of Solid State Lighting (SSL) Products, which is incorporated by reference herein in its entirety for all purposes. A point representing the CIE Standard Illuminant D65 is also shown on the diagram. The D65 illuminant is intended to represent average daylight and has a CCT of approximately 6500K and the spectral power distribution is described more fully in Joint ISO/CIE Standard, ISO 10526:1999/CIE 5005/E-1998, CIE Standard Illuminants for Colorimetry, which is incorporated by reference herein in its entirety for all purposes.

The light emitted by a light source may be represented by a point on a chromaticity diagram, such as the 1931 CIE chromaticity diagram, having color coordinates denoted (ccx, ccy) on the X-Y axes of the diagram. A region on a chromaticity diagram may represent light sources having similar chromaticity coordinates.

The ability of a light source to accurately reproduce color in illuminated objects can be characterized using the color rendering index ("CRI"), also referred to as the CIE Ra value. The Ra value of a light source is a modified average of the relative measurements of how the color rendition of an illumination system compares to that of a reference black-body radiator or daylight spectrum when illuminating eight reference colors R1-R8. Thus, the Ra value is a relative measure of the shift in surface color of an object when lit by a particular lamp. The Ra value equals 100 if the color coordinates of a set of test colors being illuminated by the illumination system are the same as the coordinates of the same test colors being irradiated by a reference light source of equivalent CCT. For CCTs less than 5000K, the reference illuminants used in the CRI calculation procedure are the SPDs of blackbody radiators; for CCTs above 5000K, imaginary SPDs calculated from a mathematical model of daylight are used. These reference sources were selected to approximate incandescent lamps and daylight, respectively. Daylight generally has an Ra value of nearly 100, incandescent bulbs have an Ra value of about 95, fluorescent lighting typically has an Ra value of about 70 to 85, while monochromatic light sources have an Ra value of essentially zero. Light sources for general illumination applications with an Ra value of less than 50 are generally considered very poor and are typically only used in applications where economic issues preclude other alternatives. The calculation of CIE Ra values is described more fully in Commission Internationale de l'Éclairage. 1995. *Technical Report: Method of Measuring and Specifying Colour Rendering Properties of Light Sources*, CIE No. 13.3-1995. Vienna, Austria: Commission Internationale de l'Éclairage, which is incorporated by reference herein in its entirety for all purposes. In addition to the Ra value, a light source can also be evaluated based on a measure of its ability to render a saturated red reference color R9 with the R9 color rendering value ("R9 value"). Light sources can further be evaluated by calculating the gamut area index ("GAP"). Connecting the rendered color points from the determination of the CIE Ra value in two dimensional space will form a gamut area. Gamut area index is calculated by dividing the gamut area formed by the light source with the gamut area formed by a reference source using the same set of colors that are used for CRI. GAI uses an Equal Energy Spectrum as the reference source rather than a black body radiator. A gamut area index related to a black body radiator ("GAIBB") can be calculated by using the gamut area formed by the blackbody radiator at the equivalent CCT to the light source.

In some aspects the present disclosure relates to lighting devices and methods to provide light having particular vision energy and circadian energy performance. Many figures of merit are known in the art, some of which are described in Ji Hye Oh, Su Ji Yang and Young Rag Do, "Healthy, natural, efficient and tunable lighting: four-package white LEDs for optimizing the circadian effect, color quality and vision performance," Light: Science & Applications (2014) 3: e141-e149, which is incorporated herein in its entirety, including supplementary information, for all purposes. Luminous efficacy of radiation ("LER") can be calculated from the ratio of the luminous flux to the radiant flux $(S(\lambda))$, i.e. the spectral power distribution of the light source being evaluated, with the following equation:

$$LER\left(\frac{lm}{W}\right) = 683\left(\frac{lm}{W}\right)\frac{\int V(\lambda)S(\lambda)d\lambda}{\int S(\lambda)d\lambda}.$$

Circadian efficacy of radiation ("CER") can be calculated from the ratio of circadian luminous flux to the radiant flux, with the following equation:

$$CER\left(\frac{blm}{W}\right) = 683\left(\frac{blm}{W}\right)\frac{\int C(\lambda)S(\lambda)d\lambda}{\int S(\lambda)d\lambda}.$$

Circadian action factor ("CAF") can be defined by the ratio of CER to LER, with the following equation:

$$F\left(\frac{blm}{lm}\right) = \frac{CER\left(\frac{blm}{W}\right)}{LER\left(\frac{lm}{W}\right)}.$$

The term "blm" refers to biolumens, units for measuring circadian flux, also known as circadian lumens. The term "1 m" refers to visual lumens. $V(\lambda)$ is the photopic spectral luminous efficiency function and $C(\lambda)$ is the circadian spectral sensitivity function. The calculations herein use the circadian spectral sensitivity function, $C(\lambda)$, from Gall et al., Proceedings of the CIE Symposium 2004 on Light and Health: Non-Visual Effects, 30 Sep.-2 Oct. 2004; Vienna, Austria 2004. CIE: Wien, 2004, pp 129-132, which is incorporated herein in its entirety for all purposes. By integrating the amount of light (milliwatts) within the circadian spectral sensitivity function and dividing such value by the number of photopic lumens, a relative measure of melatonin suppression effects of a particular light source can be obtained. A scaled relative measure denoted as melatonin suppressing milliwatts per hundred lumens may be obtained by dividing the photopic lumens by 100. The term "melatonin suppressing milliwatts per hundred lumens" consistent with the foregoing calculation method is used throughout this application and the accompanying figures and tables.

In some exemplary implementations, the present disclosure provides semiconductor light emitting devices 100 that include a plurality of LED strings, with each LED string having a recipient luminophoric medium that comprises a luminescent material. The LED(s) in each string and the luminophoric medium in each string together emit an unsaturated light having a color point within a color range in the 1931 CIE chromaticity diagram. A "color range" in the 1931 CIE chromaticity diagram refers to a bounded area defining a group of color coordinates (ccx, ccy).

In some implementations, four LED strings (101A/101B/101C/101D) are present in a device 100, and the LED strings can have recipient luminophoric mediums (102A/102B/102C/102D). A first LED string 101A and a first luminophoric medium 102A together can emit a first light having a first color point within a blue color range. The combination of the first LED string 101A and the first luminophoric medium 102A are also referred to herein as a "blue channel." A second LED string 101B and a second luminophoric medium 102B together can emit a second light having a second color point within a red color range. The combination of the second LED string 101A and the second luminophoric medium 102A are also referred to herein as a "red channel." A third LED string 101C and a third luminophoric medium 102C together can emit a third light having a third color point within a yellow/green color range. The combination of the third LED string 101A and the third luminophoric medium 102A are also referred to herein as a "yellow/green channel." A fourth LED string 101D and a fourth luminophoric medium 102D together can emit a fourth light having a fourth color point within a cyan color range. The combination of the fourth LED string 101A and the fourth luminophoric medium 102A are also referred to herein as a "cyan channel." The first, second, third, and fourth LED strings 101A/101B/101C/101D can be provided with independently applied on-state drive currents in order to tune the intensity of the first, second, third, and fourth unsaturated light produced by each string and luminophoric medium together. By varying the drive currents in a controlled manner, the color coordinate (ccx, ccy) of the total light that is emitted from the device 100 can be tuned. In some implementations, the device 100 can provide light at substantially the same color coordinate with different spectral power distribution profiles, which can result in different light characteristics at the same CCT. In some implementations, white light can be generated in modes that only produce light from two or three of the LED strings. In one implementation, white light is generated using only the first, second, and third LED strings, i.e. the blue, red, and yellow/green channels. In another implementation, white light is generated using only the first, second, and fourth LED strings, i.e., the blue, red, and cyan channels. In some implementations, only two of the LED strings are producing light during the generation of white light, as the other two LED strings are not necessary to generate white light at the desired color point with the desired color rendering performance.

In some implementations, the first color point within a blue color range can be generated using a first LED string driven by a plurality of blue LEDs with at least two different peak emission wavelengths. In some preferred implementations, two different blue LEDs are used in the device, having 1931 CIE chromaticity diagram color points of (0.1574, 0.0389) and (0.1310, 0.0651) and having peak emission wavelengths of approximately 450 nm to approximately 455 nm and approximately 460 nm to approximately 465 nm, respectively. In some implementations two or more different LEDs in the first LED string can utilize different recipient luminophoric mediums. In other implementations, two or more different LEDs in the first LED string can utilize a common recipient luminophoric medium. The plurality of LEDs and the one or more recipient luminophoric mediums can generate a combined emission of a blue color point within the suitable ranges 301A-C described elsewhere herein.

Figure 4B:
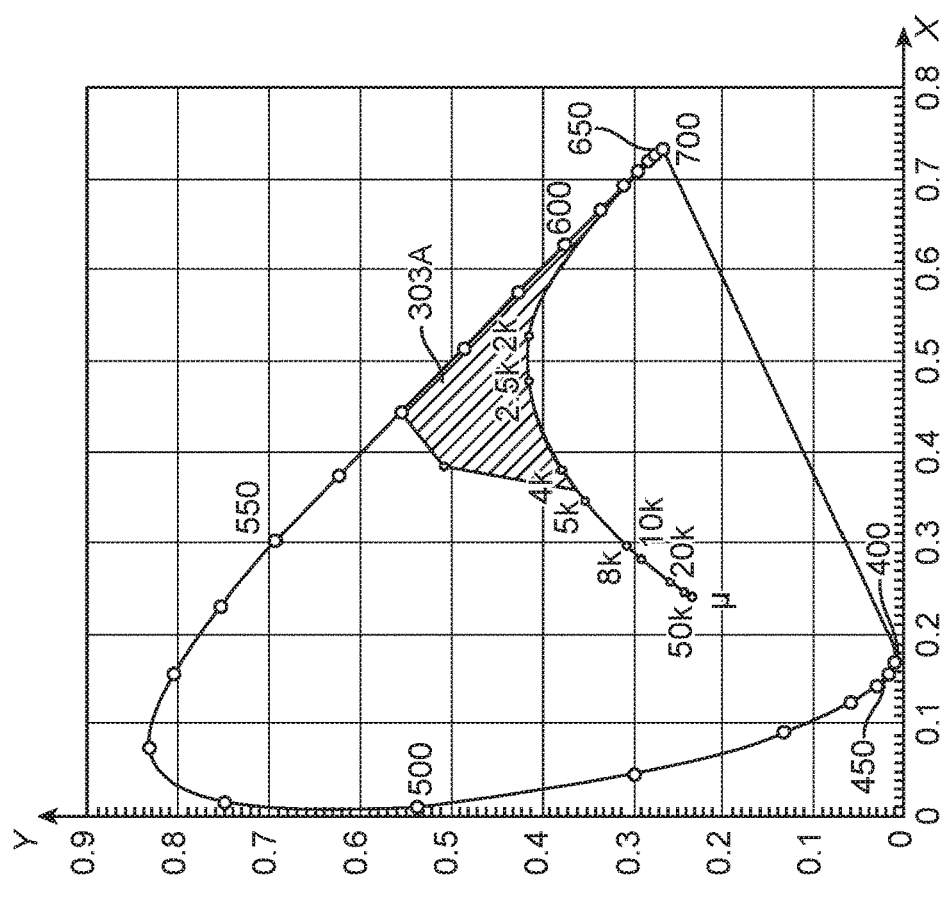
FIGS. 4A-4D illustrate some aspects of light emitting devices according to the present disclosure, including some suitable color ranges for light generated by components of the devices.
Figure 4A:
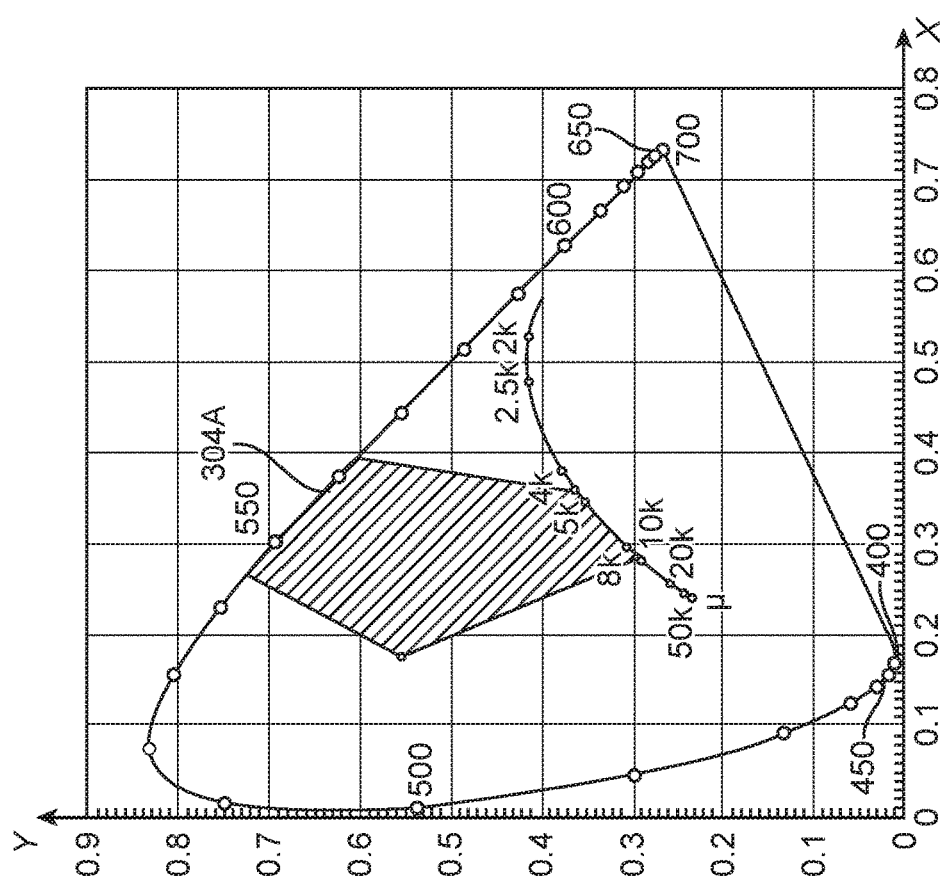
Figure 4D:
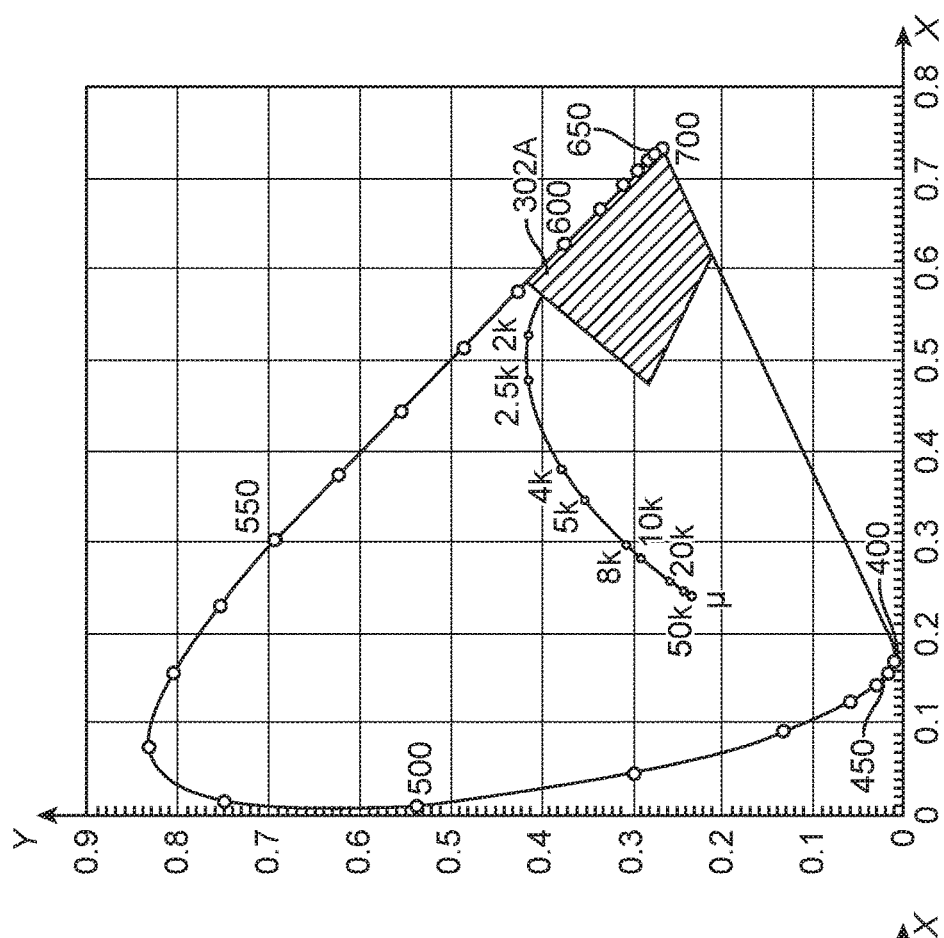
Figure 4C:
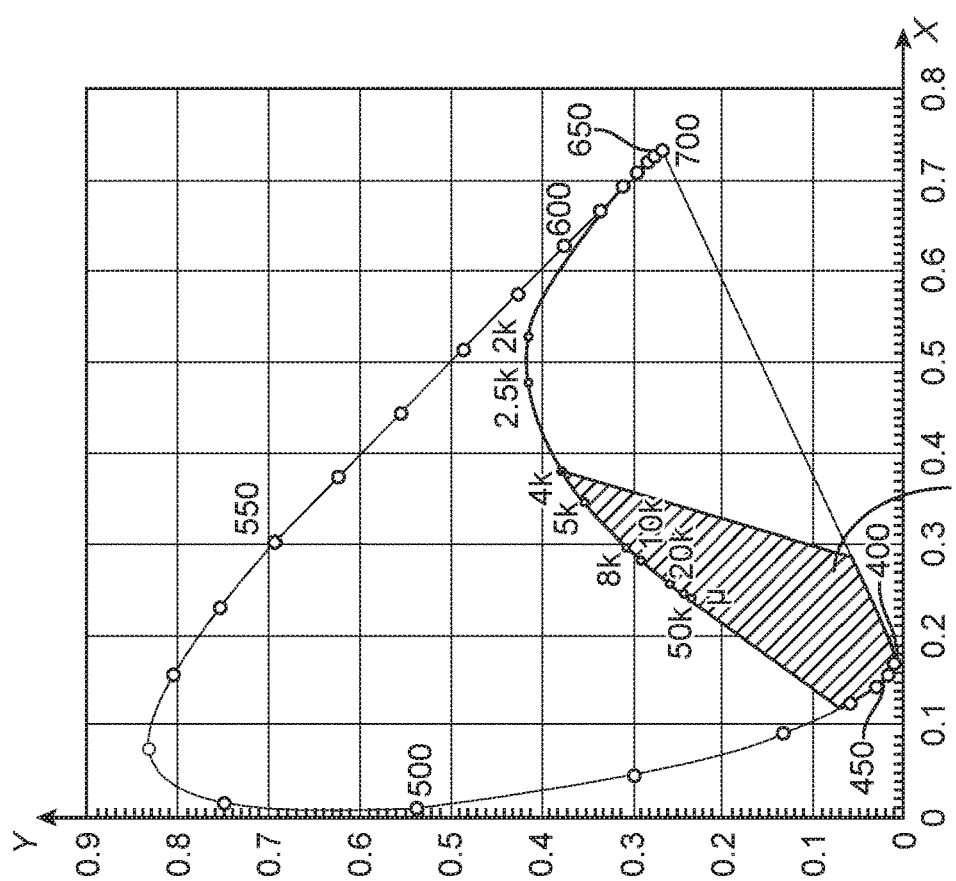

FIGS. 4A, 4B, 4C, and 4D depict suitable color ranges for some implementations of the disclosure. FIG. 4A depicts a cyan color range 304A defined by a line connecting the ccx, ccy color coordinates (0.18, 0.55) and (0.27, 0.72), the constant CCT line of 9000K, the Planckian locus between 9000K and 4600K, the constant CCT line of 4600K, and the spectral locus. FIG. 4B depicts a yellow/green color range 303A defined by the constant CCT line of 4600K, the Planckian locus between 4600K and 550K, the spectral locus, and a line connecting the ccx, ccy color coordinates (0.445, 0.555) and (0.38, 0.505). FIG. 4C depicts a blue color range 301A defined by a line connecting the ccx, ccy color coordinates of the infinity point of the Planckian locus (0.242, 0.24) and (0.12, 0.068), the Planckian locus from 4000K and infinite CCT, the constant CCT line of 4000K, the line of purples, and the spectral locus. FIG. 4D depicts a red color range 302A defined by the spectral locus between the constant CCT line of 1600K and the line of purples, the line of purples, a line connecting the ccx, ccy color coordinates (0.61, 0.21) and (0.47, 0.28), and the constant CCT line of 1600K. It should be understood that any gaps or openings in the described boundaries for the color ranges 301A, 302A, 303A, 304A should be closed with straight lines to connect adjacent endpoints in order to define a closed boundary for each color range.

Figure 5:
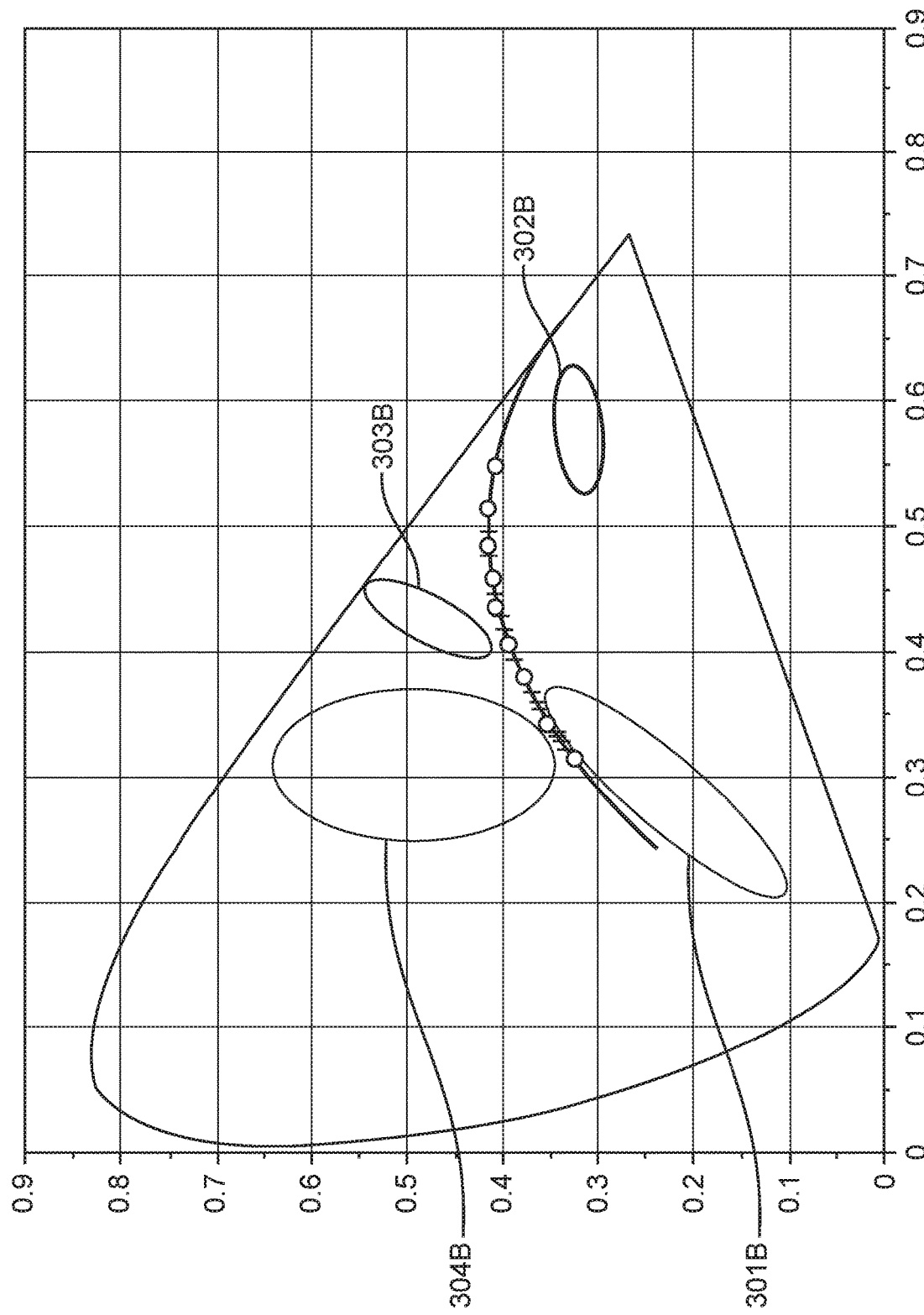
FIG. 5 illustrates some aspects of light emitting devices according to the present disclosure, including some suitable color ranges for light generated by components of the devices.
Figure 6:
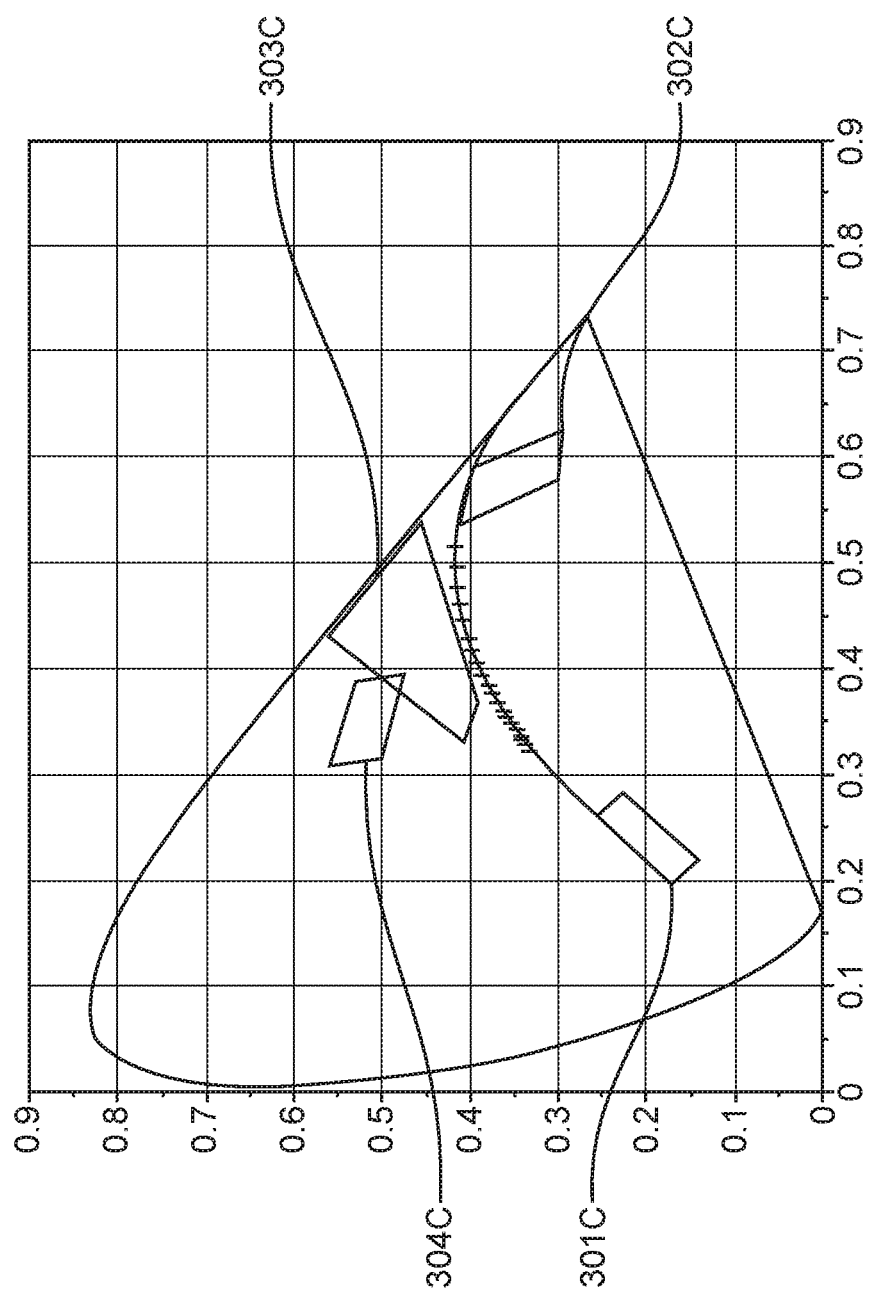
FIG. 6 illustrates some aspects of light emitting devices according to the present disclosure, including some suitable color ranges for light generated by components of the devices.

In some implementations, suitable color ranges can be narrower than those depicted in FIGS. 4A-4D. FIG. 5 depicts some suitable color ranges for some implementations of the disclosure. A blue color range 301B can be defined by a 60-step MacAdam ellipse at a CCT of 20000K, 40 points below the Planckian locus. A red color range 302B can be defined by a 20-step MacAdam ellipse at a CCT of 1200K, 20 points below the Planckian locus. A yellow/green color range 303B can be defined by a 16-step MacAdam ellipse at a CCT of 3700K, 30 points above Planckian locus. A cyan color range 304B can be defined by 30-step MacAdam ellipse at a CCT of 6000K, 68 points above the Planckian locus. FIG. 6 depicts some further color ranges suitable for some implementations of the disclosure: blue color range 301C, red color range 302C, yellow/green color range 303C, and cyan color range 304C.

In some implementations, the LEDs in the first, second, third and fourth LED strings can be LEDs with peak emission wavelengths at or below about 535 nm. In some implementations, the LEDs emit light with peak emission wavelengths between about 360 nm and about 535 nm. In some implementations, the LEDs in the first, second, third and fourth LED strings can be formed from InGaN semiconductor materials. In some preferred implementations, the first, second, and third LED strings can have LEDs having a peak wavelength between about 405 nm and about 485 nm. In some implementations the fourth LED string can have LEDs having a peak wavelength between about 485 nm and about 520 nm. The LEDs used in the first, second, third, and fourth LED strings may have full-width half-maximum wavelength ranges of between about 10 nm and about 30 nm. In some preferred implementations, the first, second, and third LED strings can include one or more LUXEON Z Color Line royal blue LEDs (product code LXZ1-PR01) of color bin codes 3, 4, 5, or 6 or one or more LUXEON Z Color Line blue LEDs (LXZ1-PB01) of color bin code 1 or 2 (Lumileds Holding B.V., Amsterdam, Netherlands). In some preferred implementations, the fourth LED string can have one or more LUXEON Z Color Line blue LEDs (LXZ1-PB01) of color bin code 5 or one or more LUXEON Z Color Line cyan LEDs (LXZ1-PE01) color bin code 1, 2, 6, 7, 8, or 9 (Lumileds Holding B.V., Amsterdam, Netherlands). The wavelength information for these color bins is provided in the table in FIG. 14. Similar LEDs from other manufacturers such as OSRAM GmbH and Cree, Inc. could also be used, provided they have peak emission and full-width half-maximum wavelengths of the appropriate values.

In implementations utilizing LEDs that emit substantially saturated light at wavelengths between about 360 nm and about 535 nm, the device 100 can include suitable recipient luminophoric mediums for each LED in order to produce light having color points within the suitable blue color ranges 301A-C, red color ranges 302A-C, yellow/green color ranges 303A-C, and cyan color ranges 304A-C described herein. The light emitted by each LED string, i.e., the light emitted from the LED(s) and associated recipient luminophoric medium together, can have a spectral power distribution ("SPD") having spectral power with ratios of power across the visible wavelength spectrum from about 380 nm to about 780 nm. While not wishing to be bound by any particular theory, it is speculated that the use of such LEDs in combination with recipient luminophoric mediums to create unsaturated light within the suitable color ranges 301A-C, 302A-C, 303A-C, and 304A-C provides for improved color rendering performance for white light across a predetermined range of CCTs from a single device 100. Some suitable ranges for spectral power distribution ratios of the light emitted by the four LED strings (101A/101B/101C/101D) and recipient luminophoric mediums (102A/102B/102C/102D) together are shown in FIGS. 7 and 8. The figures show the ratios of spectral power within wavelength ranges, with an arbitrary reference wavelength range selected for each color range and normalized to a value of 100.0. FIGS. 7 and 8 show suitable minimum and maximum values for the spectral intensities within various ranges relative to the normalized range with a value of 100.0, for the color points within the blue, cyan, yellow/green ("yag"), and red color ranges. While not wishing to be bound by any particular theory, it is speculated that because the spectral power distributions for generated light with color points within the blue, cyan, and yellow/green color ranges contains higher spectral intensity across visible wavelengths as compared to lighting apparatuses and methods that utilize more saturated colors, this allows for improved color rendering for test colors other than R1-R8.

Blends of luminescent materials can be used in luminophoric mediums (102A/102B/102C/102D) to create luminophoric mediums having the desired saturated color points when excited by their respective LED strings (101A/101B/101C/101D) including luminescent materials such as those disclosed in co-pending application PCT/US2016/015318 filed Jan. 28, 2016, entitled "Compositions for LED light conversion," the entirety of which is hereby incorporated by this reference as if sully set forth herein. Traditionally, a desired combined output light can be generated along a tie line between the LED string output light color point and the saturated color point of the associated recipient luminophoric medium by utilizing different ratios of total luminescent material to the encapsulant material in which it is incorporated. Increasing the amount of luminescent material in the optical path will shift the output light color point towards the saturated color point of the luminophoric medium. In some instances, the desired saturated color point of a recipient luminophoric medium can be achieved by blending two or more luminescent materials in a ratio. The appropriate ratio to achieve the desired saturated color point can be determined via methods known in the art. Generally speaking, any blend of luminescent materials can be treated as if it were a single luminescent material, thus the ratio of luminescent materials in the blend can be adjusted to continue to meet a target CIE value for LED strings having different peak emission wavelengths. Luminescent materials can be tuned for the desired excitation in response to the selected LEDs used in the LED strings (101A/101B/101C/101D), which may have different peak emission wavelengths within the range of from about 360 nm to about 535 nm. Suitable methods for tuning the response of luminescent materials are known in the art and may include altering the concentrations of dopants within a phosphor, for example.

In some implementations of the present disclosure, luminophoric mediums can be provided with combinations of two types of luminescent materials. The first type of luminescent material emits light at a peak emission between about 515 nm and about 590 nm in response to the associated LED string emission. The second type of luminescent material emits at a peak emission between about 590 nm and about 700 nm in response to the associated LED string emission. In some instances, the luminophoric mediums disclosed herein can be formed from a combination of at least one luminescent material of the first and second types described in this paragraph. In implementations, the luminescent materials of the first type can emit light at a peak emission at about 515 nm, 525 nm, 530 nm, 535 nm, 540 nm, 545 nm, 550 nm, 555 nm, 560 nm, 565 nm, 570 nm, 575 nm, 580 nm, 585 nm, or 590 nm in response to the associated LED string emission. In preferred implementations, the luminescent materials of the first type can emit light at a peak emission between about 520 nm to about 555 nm. In implementations, the luminescent materials of the second type can emit light at a peak emission at about 590 nm, about 595 nm, 600 nm, 605 nm, 610 nm, 615 nm, 620 nm, 625 nm, 630 nm, 635 nm, 640 nm, 645 nm, 650 nm, 655 nm, 670 nm, 675 nm, 680 nm, 685 nm, 690 nm, 695 nm, or 670 nm in response to the associated LED string emission. In preferred implementations, the luminescent materials of the first type can emit light at a peak emission between about 600 nm to about 670 nm. Some exemplary luminescent materials of the first and second type are disclosed elsewhere herein and referred to as Compositions A-F. Table 1 shows aspects of some exemplar luminescent materials and properties:

TABLE 1

| Designator | Exemplary Material(s) | Density (g/mL) | Emission Peak (nm) | FWHM (nm) | Emission Peak Range (nm) | FWHM Range (nm) |
|---|---|---|---|---|---|---|
| Composition "A" | Luag: Cerium doped lutetium aluminum garnet ($Lu_3Al_5O_{12}$) | 6.73 | 535 | 95 | 530-540 | 90-100 |
| Composition "B" | Yag: Cerium doped yttrium aluminum garnet ($Y_3Al_5O_{12}$) | 4.7 | 550 | 110 | 545-555 | 105-115 |
| Composition "C" | a 650 nm-peak wavelength emission phosphor: Europium doped calcium aluminum silica nitride ($CaAlSiN_3$) | 3.1 | 650 | 90 | 645-655 | 85-95 |
| Composition "D" | a 525 nm-peak wavelength emission phosphor: GBAM: $BaMgAl_{10}O_{17}$: Eu | 3.1 | 525 | 60 | 520-530 | 55-65 |
| Composition "E" | a 630 nm-peak wavelength emission quantum dot: any semiconductor quantum dot material of appropriate size for desired emission wavelengths | 5.1 | 630 | 40 | 625-635 | 35-45 |
| Composition "F" | a 610 nm-peak wavelength emission quantum dot: any semiconductor quantum dot material of appropriate size for desired emission wavelengths | 5.1 | 610 | 40 | 605-615 | 35-45 |

Blends of Compositions A-F can be used in luminophoric mediums (102A/102B/102C/102D) to create luminophoric mediums having the desired saturated color points when excited by their respective LED strings (101A/101B/101C/101D). In some implementations, one or more blends of one or more of Compositions A-F can be used to produce luminophoric mediums (102A/102B/102C/102D). In some preferred implementations, one or more of Compositions A, B, and D and one or more of Compositions C, E, and F can be combined to produce luminophoric mediums (102A/102B/102C/102D). In some preferred implementations, the encapsulant for luminophoric mediums (102A/102B/102C/102D) comprises a matrix material having density of about 1.1 mg/mm$^3$ and refractive index of about 1.545. Suitable matrix materials can have refractive indices of about 1.4 to about 1.6. In some implementations, Composition A can have a refractive index of about 1.82 and a particle size from about 18 micrometers to about 40 micrometers. In some implementations, Composition B can have a refractive index of about 1.84 and a particle size from about 13 micrometers to about 30 micrometers. In some implementations, Composition C can have a refractive index of about 1.8 and a particle size from about 10 micrometers to about 15 micrometers. In some implementations, Composition D can have a refractive index of about 1.8 and a particle size from about 10 micrometers to about 15 micrometers. Suitable phosphor materials for Compositions A, B, C, and D are commercially available from phosphor manufacturers such as Mitsubishi Chemical Holdings Corporation (Tokyo, Japan), Intematix Corporation (Fremont, Calif.), EMD Performance Materials of Merck KGaA (Darmstadt, Germany), and PhosphorTech Corporation (Kennesaw, Ga.).

In some aspects, the present disclosure provides methods of generating white light with tunable circadian energy performance. The methods can comprise producing light from the blue, red, yellow/green, and cyan channels described herein, in various combinations of two or more of the channels at any given time. Substantially the same white light, in terms of position on the 1931 CIE chromaticity diagram, can be generated in two or more light emitting modes. White light can be generated within a 7-step MacAdam ellipse of a plurality of target CCTs selected from between 1800K and 4200K via a plurality of emitting modes, the emitting modes comprising a first emitting mode, wherein the method comprises producing light from the first, second, third, and fourth LED strings; a second emitting mode, wherein the method comprises producing light from the first, second, and third LED strings but not the fourth LED string; and a third emitting mode, wherein the method comprises producing light from the first, second, and fourth LED strings but not the third LED string. For a particular target CCT, the white light generated in two of the light emitting modes can be within about 0.1, about 0.2, about 0.3, about 0.4, about 0.5, about 0.6, about 0.7, about 0.8, about 0.9, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, or between about 8.0 and about 10.0 standard deviations of color matching (SDCM). In preferred embodiments, the white light generated in two of the light emitting modes at a target CCT is within about 0.1 to about 3.0 SDCM. In further preferred embodiments, the white light generated in two of the light emitting modes at a target CCT is within about 0.1 to about 1.0 SDCM, or more preferably within about 0.1 to about 0.5 SDCM. For each target CCT, the respective circadian action factor values of the white light generated in any two of the first, second, and third emitting modes differ from each other by a predetermined threshold amount. The predetermined threshold amount may be at least about 5%, 10%, 15%, 20% 25%, 30%, 35%, 40%, 50%, 60%, 70%, 80%, 100%, 125%, 150%, 200%, 300%, 400%, or more. In some implementations, the circadian energy tuning can be achieved between emitting modes while generating white light corresponding to a plurality of points along a pre-defined path within 7-step MacAdam ellipse of the Planckian locus with the light generated at each point having one or more of Ra≥80, R9≥50, and GAIBB≥90.

EXAMPLES

General Simulation Method

Devices having four LED strings with particular color points were simulated. For each device, LED strings and recipient luminophoric mediums with particular emissions were selected, and then white light rendering capabilities were calculated for a select number of representative points on or near the Planckian locus between about 1800K and 10000K. The CIE Ra value, R9 value, GAI, and GAIBB were calculated at each representative point, along with circadian energy performance metrics.

The calculations were performed with Scilab (Scilab Enterprises, Versailles, France), LightTools (Synopsis, Inc., Mountain View, Calif.), and custom software created using Python (Python Software Foundation, Beaverton, Oreg.). Each LED string was simulated with an LED emission spectrum and excitation and emission spectra of luminophoric medium(s). For luminophoric mediums comprising phosphors, the simulations also included the absorption spectrum and particle size of phosphor particles. The LED strings generating combined emissions within blue, red and yellow/green color regions were prepared using spectra of a LUXEON Z Color Line royal blue LED (product code LXZ1-PR01) of color bin codes 3, 4, 5, or 6 or a LUXEON Z Color Line blue LED (LXZ1-PB01) of color bin code 1 or 2 (Lumileds Holding B.V., Amsterdam, Netherlands). The LED strings generating combined emissions with color points within the cyan regions were prepared using spectra of a LUXEON Z Color Line blue LED (LXZ1-PB01) of color bin code 5 or LUXEON Z Color Line cyan LED (LXZ1-PE01) color bin code 1, 8, or 9 (Lumileds Holding B.V., Amsterdam, Netherlands). FIG. 14 shows emission characteristics of selected LEDs from Lumileds. Similar LEDs from other manufacturers such as OSRAM GmbH and Cree, Inc. could also be used.

The emission, excitation and absorption curves are available from commercially available phosphor manufacturers such as Mitsubishi Chemical Holdings Corporation (Tokyo, Japan), Intematix Corporation (Fremont, Calif.), EMD Performance Materials of Merck KGaA (Darmstadt, Germany), and PhosphorTech Corporation (Kennesaw, Ga.). The luminophoric mediums used in the LED strings were combinations of one or more of Compositions A, B, and D and one or more of Compositions C, E, and F as described more fully elsewhere herein. Those of skill in the art appreciate that various combinations of LEDs and phosphor blends can be combined to generate combined emissions with desired color points on the 1931 CIE chromaticity diagram and the desired spectral power distributions.

Example 1

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue color point with a 1931 CIE chromaticity diagram color point of (0.2625, 0.1763). A second LED string is driven by a blue LED having peak emission wavelength of approximately 450 nm to approximately 455 nm, utilizes a recipient luminophoric medium, and generates a combined emission of a red color point with a 1931 CIE chromaticity diagram color point of (0.5842, 0.3112). A third LED string is driven by a blue LED having peak emission wavelength of approximately 450 nm to approximately 455 nm, utilizes a recipient luminophoric medium, and generates a combined emission of a yellow/green color point with a 1931 CIE chromaticity diagram color point of (0.4482, 0.5258). A fourth LED string is driven by a cyan LED having a peak emission wavelength of approximately 505 nm, utilizes a recipient luminophoric medium, and generates a combined emission of a cyan color point with a 1931 CIE chromaticity diagram color point of (0.3258, 0.5407). FIGS. 9A-9C shows color-rendering characteristics of the device for a representative selection of white light color points near the Planckian locus, with data shown for white light generated in different operational modes using combinations of the first, second, third, and fourth LED strings. FIG. 9D shows comparisons of circadian action factor values for white light points generated at similar CCT values under different operational modes. Table 2 below shows the spectral power distributions for the blue, red, yellow-green, and cyan color points generated by the device of this Example, with spectral power shown within wavelength ranges in nanometers from 380 nm to 780 nm, with an arbitrary reference wavelength range selected for each color range and normalized to a value of 100.0:

Example 2

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue color point with a 1931 CIE chromaticity diagram color point of (0.2625, 0.1763). A second LED string is driven by a blue LED having peak emission wavelength of approximately 450 nm to approximately 455 nm, utilizes a recipient luminophoric medium, and generates a combined emission of a red color point with a 1931 CIE chromaticity diagram color point of (0.5842, 0.3112). A third LED string is driven by a blue LED having peak emission wavelength of approximately 450 nm to approximately 455 nm, utilizes a recipient luminophoric medium, and generates a combined emission of a yellow/green color point with a 1931 CIE chromaticity diagram color point of (0.5108, 0.4708). A fourth LED string is driven by a cyan LED having a peak emission wavelength of approximately 505 nm, utilizes a recipient luminophoric medium, and generates a combined emission of a cyan color point with a 1931 CIE chromaticity diagram color point of (0.3258, 0.5407). FIGS. 10A-10C shows color-rendering characteristics of the device for a representative selection of white light color points near the Planckian locus, with data shown for white light generated in different operational modes using combinations of the first, second, third, and fourth LED strings. FIG. 10D shows comparisons of circadian action factor values for white light points generated at similar CCT values under different operational modes. Table 3 below shows the spectral power distributions for the blue, red, yellow-green, and cyan color points generated by the device of this Example, with spectral power shown within wavelength ranges in nanometers from 380 nm to 780 nm, with an arbitrary reference wavelength range selected for each color range and normalized to a value of 100.0:

TABLE 2

| | 380-420 | 421-460 | 461-500 | 501-540 | 541-580 | 581-620 | 621-660 | 661-700 | 701-740 | 741-780 |
|---|---|---|---|---|---|---|---|---|---|---|
| Blue | 0.4 | 100.0 | 20.9 | 15.2 | 25.3 | 26.3 | 25.1 | 13.9 | 5.2 | 1.6 |
| Red | 0.0 | 9.6 | 2.0 | 1.4 | 9.0 | 48.5 | 100.0 | 73.1 | 29.5 | 9.0 |
| Yellow-Green | 1.0 | 1.1 | 5.7 | 75.8 | 100.0 | 83.6 | 69.6 | 40.9 | 15.6 | 4.7 |
| Cyan | 0.1 | 0.5 | 53.0 | 100.0 | 65.0 | 41.6 | 23.1 | 11.6 | 4.2 | 0.6 |

TABLE 3

|  | 380-420 | 421-460 | 461-500 | 501-540 | 541-580 | 581-620 | 621-660 | 661-700 | 701-740 | 741-780 |
|---|---|---|---|---|---|---|---|---|---|---|
| Blue | 0.3 | 100.0 | 196.1 | 33.0 | 40.3 | 38.2 | 34.2 | 20.4 | 7.8 | 2.3 |
| Red | 0.0 | 157.8 | 2.0 | 1.4 | 9.0 | 48.5 | 100.0 | 73.1 | 29.5 | 9.0 |
| Yellow-Green | 0.0 | 1.0 | 4.2 | 56.6 | 100.0 | 123.4 | 144.9 | 88.8 | 34.4 | 10.5 |
| Cyan | 0.1 | 0.5 | 53.0 | 100.0 | 65.0 | 41.6 | 23.1 | 11.6 | 4.2 | 0.6 |

Example 3

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue color point with a 1931 CIE chromaticity diagram color point of (0.2219, 0.1755). A second LED string is driven by a blue LED having peak emission wavelength of approximately 450 nm to approximately 455 nm, utilizes a recipient luminophoric medium, and generates a combined emission of a red color point with a 1931 CIE chromaticity diagram color point of (0.5702, 0.3869). A third LED string is driven by a blue LED having peak emission wavelength of approximately 450 nm to approximately 455 nm, utilizes a recipient luminophoric medium, and generates a combined emission of a yellow/green color point with a 1931 CIE chromaticity diagram color point of (0.3722, 0.4232). A fourth LED string is driven by a cyan LED having a peak emission wavelength of approximately 505 nm, utilizes a recipient luminophoric medium, and generates a combined emission of a cyan color point with a 1931 CIE chromaticity diagram color point of (0.3704, 0.5083). FIGS. 11A-11C shows color-rendering characteristics of the device for a representative selection of white light color points near the Planckian locus, with data shown for white light generated in different operational modes using combinations of the first, second, third, and fourth LED strings. FIG. 11D shows comparisons of circadian action factor values for white light points generated at similar CCT values under different operational modes. Table 4 below shows the spectral power distributions for the blue, red, yellow-green, and cyan color points generated by the device of this Example, with spectral power shown within wavelength ranges in nanometers from 380 nm to 780 nm, with an arbitrary reference wavelength range selected for each color range and normalized to a value of 100.0:

TABLE 4

|  | 380-420 | 421-460 | 461-500 | 501-540 | 541-580 | 581-620 | 621-660 | 661-700 | 701-740 | 741-780 |
|---|---|---|---|---|---|---|---|---|---|---|
| Blue | 8.1 | 100.0 | 188.1 | 35.6 | 40.0 | 70.0 | 80.2 | 12.4 | 2.3 | 1.0 |
| Red | 0.7 | 2.1 | 4.1 | 12.2 | 20.5 | 51.8 | 100.0 | 74.3 | 29.3 | 8.4 |
| Yellow-Green | 1.0 | 25.3 | 52.7 | 77.5 | 100.0 | 80.5 | 62.0 | 35.1 | 13.3 | 4.0 |
| Cyan | 0.4 | 1.5 | 55.5 | 100.0 | 65.3 | 59.9 | 57.1 | 35.0 | 13.5 | 4.1 |

Example 4

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue color point with a 1931 CIE chromaticity diagram color point of (0.2387, 0.1692). A second LED string is driven by a blue LED having peak emission wavelength of approximately 450 nm to approximately 455 nm, utilizes a recipient luminophoric medium, and generates a combined emission of a red color point with a 1931 CIE chromaticity diagram color point of (0.5563, 0.3072). A third LED string is driven by a blue LED having peak emission wavelength of approximately 450 nm to approximately 455 nm, utilizes a recipient luminophoric medium, and generates a combined emission of a yellow/green color point with a 1931 CIE chromaticity diagram color point of (0.4494, 0.5161). A fourth LED string is driven by a cyan LED having a peak emission wavelength of approximately 505 nm, utilizes a recipient luminophoric medium, and generates a combined emission of a cyan color point with a 1931 CIE chromaticity diagram color point of (0.3548, 0.5484). FIGS. 12A-12C shows color-rendering characteristics of the device for a representative selection of white light color points near the Planckian locus, with data shown for white light generated in different operational modes using combinations of the first, second, third, and fourth LED strings. FIG. 12D shows comparisons of circadian action factor values for white light points generated at similar CCT values under different operational modes. Table 5 below shows the spectral power distributions for the blue, red, yellow-green, and cyan color points generated by the device of this Example, with spectral power shown within wavelength ranges in nanometers from 380 nm to 780 nm, with an arbitrary reference wavelength range selected for each color range and normalized to a value of 100.0:

TABLE 5

|  | 380-420 | 421-460 | 461-500 | 501-540 | 541-580 | 581-620 | 621-660 | 661-700 | 701-740 | 741-780 |
|---|---|---|---|---|---|---|---|---|---|---|
| Blue | 1.9 | 100.0 | 34.4 | 32.1 | 40.5 | 29.0 | 15.4 | 5.9 | 2.8 | 1.5 |
| Red | 14.8 | 10.5 | 6.7 | 8.7 | 8.7 | 102.8 | 100.0 | 11.0 | 1.5 | 1.1 |
| Yellow-Green | 1.1 | 2.3 | 5.9 | 61.0 | 100.0 | 85.0 | 51.0 | 12.6 | 3.2 | 1.0 |
| Cyan | 0.7 | 1.6 | 39.6 | 100.0 | 80.4 | 53.0 | 24.9 | 9.5 | 3.3 | 1.2 |

Example 5

A semiconductor light emitting device was simulated having four LED strings. A first LED string is driven by a blue LED having peak emission wavelength of approximately 450 nm to approximately 455 nm, utilizes a recipient luminophoric medium, and generates a combined emission of a blue color point with a 1931 CIE chromaticity diagram color point of (0.2524, 0.223). A second LED string is driven by a blue LED having peak emission wavelength of approximately 450 nm to approximately 455 nm, utilizes a recipient luminophoric medium, and generates a combined emission of a red color point with a 1931 CIE chromaticity diagram color point of (0.5941, 0.3215). A third LED string is driven by a blue LED having peak emission wavelength of approximately 450 nm to approximately 455 nm, utilizes a recipient luminophoric medium, and generates a combined emission of a yellow/green color point with a 1931 CIE chromaticity diagram color point of (0.4338, 0.5195). A fourth LED string is driven by a cyan LED having a peak emission wavelength of approximately 505 nm, utilizes a recipient luminophoric medium, and generates a combined emission of a cyan color point with a 1931 CIE chromaticity diagram color point of (0.3361, 0.5257). FIGS. 13A-13C shows color-rendering characteristics of the device for a representative selection of white light color points near the Planckian locus, with data shown for white light generated in different operational modes using combinations of the first, second, third, and fourth LED strings. FIG. 13D shows comparisons of circadian action factor values for white light points generated at similar CCT values under different operational modes. Table 6 below shows the spectral power distributions for the blue, red, yellow-green, and cyan color points generated by the device of this Example, with spectral power shown within wavelength ranges in nanometers from 380 nm to 780 nm, with an arbitrary reference wavelength range selected for each color range and normalized to a value of 100.0:

TABLE 6

|  | 380-420 | 421-460 | 461-500 | 501-540 | 541-580 | 581-620 | 621-660 | 661-700 | 701-740 | 741-780 |
|---|---|---|---|---|---|---|---|---|---|---|
| Blue | 1.9 | 100.0 | 34.4 | 32.1 | 40.5 | 29.0 | 15.4 | 5.9 | 2.8 | 1.5 |
| Red | 0.2 | 8.5 | 3.0 | 5.5 | 9.5 | 60.7 | 100.0 | 1.8 | 0.5 | 0.3 |
| Yellow-Green | 0.8 | 5.6 | 6.3 | 73.4 | 100.0 | 83.8 | 48.4 | 19.5 | 6.5 | 2.0 |
| Cyan | 0.2 | 1.4 | 58.6 | 100.0 | 62.0 | 47.5 | 28.2 | 6.6 | 1.8 | 0.6 |

Those of ordinary skill in the art will appreciate that a variety of materials can be used in the manufacturing of the components in the devices and systems disclosed herein. Any suitable structure and/or material can be used for the various features described herein, and a skilled artisan will be able to select an appropriate structures and materials based on various considerations, including the intended use of the systems disclosed herein, the intended arena within which they will be used, and the equipment and/or accessories with which they are intended to be used, among other considerations. Conventional polymeric, metal-polymer composites, ceramics, and metal materials are suitable for use in the various components. Materials hereinafter discovered and/or developed that are determined to be suitable for use in the features and elements described herein would also be considered acceptable.

When ranges are used herein for physical properties, such as molecular weight, or chemical properties, such as chemical formulae, all combinations, and subcombinations of ranges for specific exemplar therein are intended to be included.

The disclosures of each patent, patent application, and publication cited or described in this document are hereby incorporated herein by reference, in its entirety.

Those of ordinary skill in the art will appreciate that numerous changes and modifications can be made to the exemplars of the disclosure and that such changes and modifications can be made without departing from the spirit of the disclosure. It is, therefore, intended that the appended claims cover all such equivalent variations as fall within the true spirit and scope of the disclosure.

What is claimed:

1. A method of generating white light, the method comprising:
    producing light from a first light emitting diode ("LED") string that comprises a blue LED with peak wavelength of between about 405 nm and about 470 nm;
    producing light from a second LED string that comprises a blue LED with peak wavelength of between about 405 nm and about 470 nm;
    producing light from a third LED string that comprises a blue LED with peak wavelength of between about 405 nm and about 470 nm, a fourth LED string that comprises a cyan LED with peak wavelength of between about 485 nm and about 520 nm; and
    passing the light produced by each of the first, second, third, and fourth LED strings through one of a plurality of respective luminophoric mediums;
    wherein the light produced by the second LED string generates a red color point after passing through said one of the plurality of respective luminophoric mediums;
    wherein spectral power distribution for the red color point includes between 48.5% and 102.8% for wavelengths between 581 nm to 620 nm, 100% for wavelengths between 621 nm to 660 nm, between 1.8% to 74.3% for wavelengths between 661 nm to 700 nm, between 0.5% to 29.5% for wavelengths between 701 nm to 740 nm, and between 0.3% to 9.0% for wavelengths between 741 nm to 780 nm; and combining the light exiting each of the plurality of respective luminophoric mediums together into the white light;

wherein the white light corresponds to at least one of a plurality of points along a predefined path near the black body locus in the 1931 CIE Chromaticity Diagram.

2. The method of claim 1, wherein:

the light produced from the first LED string is passed through a first recipient luminophoric medium of the plurality of luminophoric mediums that comprises a first luminescent material, wherein the light exiting the first recipient luminophoric medium comprises unsaturated light having a first color point within a blue color range;

the light produced from the second LED string is passed through a second recipient luminophoric medium of the plurality of luminophoric mediums that comprises a second luminescent material, wherein the light exiting the second recipient luminophoric medium comprises unsaturated light having a second color point within a red color range;

the light produced from the third LED string is passed through a third recipient luminophoric medium of the plurality of luminophoric mediums that comprises a third luminescent material, wherein the light exiting the third recipient luminophoric medium comprises unsaturated light having a third color point within a yellow/green color range; and the light produced from the fourth LED string is passed through a fourth recipient luminophoric medium of the plurality of luminophoric mediums that comprises a fourth luminescent material, wherein the light exiting the fourth recipient luminophoric medium comprises unsaturated light having a fourth color point within a cyan color range.

3. The method of claim 2, wherein the blue color range is defined by a line connecting ccx, ccy color coordinates of an infinity point of a Planckian locus (0.242, 0.24) and (0.12, 0.068), a Planckian locus from 4000K and infinite CCT, a constant CCT line of 4000K, a line of purples, and a spectral locus;

the red color range is defined by the spectral locus between a constant CCT line of 1600K, the line of purples, a line connecting ccx, ccy color coordinates (0.61, 0.21) and (0.47, 0.28), and the constant CCT line of 1600K the yellow/green color range is defined by the constant CCT line of 4600K, a Planckian locus between 4600K and 550K, the spectral locus, and a line connecting ccx, ccy color coordinates (0.445, 0.555) and (0.38, 0.505);

the cyan color range is defined by a line connecting ccx, ccy color coordinates (0.18, 0.55) and (0.27, 0.72), a constant CCT line of 9000K, a Planckian locus between 9000K and 4600K, the constant CCT line of 4600K, and the spectral locus.

4. The method of claim 2, wherein the blue color range comprises a region on the 1931 CIE Chromaticity Diagram defined by a 60-step MacAdam ellipse at 20000K, 40 points below a Planckian locus.

5. The method of claim 2, wherein the red color range comprises a region on the 1931 CIE Chromaticity Diagram defined by a 20-step MacAdam ellipse at 1200K, 20 points below a Planckian locus.

6. The method of claim 2, wherein the yellow/green color range comprises a region on the 1931 CIE Chromaticity Diagram defined by a 16-step MacAdam ellipse at 3700K, 30 points above a Planckian locus.

7. The method of claim 2, wherein the cyan color range comprises a region on the 1931 CIE Chromaticity Diagram defined by 30-step MacAdam ellipse at 6000K, 68 points above a Planckian locus.

8. The method of claim 2, wherein the generated white light falls within a 7-step MacAdam ellipse around any point on the black body locus having a correlated color temperature between 1800K and 4200K; and wherein the generated white light corresponds to the plurality of points along the predefined path with the light generated at each point of the plurality of points having light with one or more of Ra≥80, R9≥50, and GAIBB≥90.

9. The method of claim 8, wherein the method further comprises generating the white light within a 7-step MacAdam ellipse of a plurality of target CCTs selected from between 1800K and 4200K via a plurality of emitting modes, the plurality of emitting modes comprising:

a first emitting mode, wherein the method comprises producing light from the first, second, third, and fourth LED strings;

a second emitting mode, wherein the method comprises producing light from the first, second, and third LED strings but not the fourth LED string; and a third emitting mode, wherein the method comprises producing light from the first, second, and fourth LED strings but not the third LED string.

10. The method of claim 9, wherein for each of the plurality of target CCTs, a respective circadian action factor values of the white light generated in any two of the first, second, and third emitting modes differ from each other by a predetermined threshold amount.

11. The method of claim 10, wherein the predetermined threshold amount is about 100%.

12. The method of claim 10, wherein the predetermined threshold amount is about 75%.

13. The method of claim 10, wherein the predetermined threshold amount is about 50%.

14. The method of claim 10, wherein the predetermined threshold amount is about 30%.

15. The method of claim 10, wherein the predetermined threshold amount is between about 5% and about 30%.

16. The method of claim 9, wherein for each of the plurality of target CCTs, the white light generated in two of the light emitting modes is within about 1.0 standard deviations of color matching (SDCM).

17. The method of claim 9, wherein for each of the plurality of target CCTs, the white light generated in two of the light emitting modes is within about 0.5 standard deviations of color matching (SDCM).

18. The method of claim 1, wherein a spectral power distribution for the red color point is between 0.0% to 14.8% for wavelengths between 380 nm to 420 nm, between 2.1% to 157.5% for wavelengths between 421 nm to 460 nm, between 2.0% to 6.7% for wavelengths between 461 nm to 500 nm, between 1.4% to 12.2% for wavelengths between 501 nm to 540 nm, between 8.7% to 20.5% for wavelengths between 541 nm to 580 nm, between 48.5% and 102.8% for wavelengths between 581 nm to 620 nm, 100% for wavelengths between 621 nm to 660 nm, between 1.8% to 74.3% for wavelengths between 661 nm to 700 nm, between 0.5% to 29.5% for wavelengths between 701 nm to 740 nm, and between 0.3% to 9.0% for wavelengths between 741 nm to 780 nm.

\* \* \* \* \*